US012569518B2

(12) United States Patent (10) Patent No.: US 12,569,518 B2
Houghton et al. (45) Date of Patent: Mar. 10, 2026

(54) CARTILAGE TISSUE

(71) Applicant: UNIVERSITY OF SOUTHAMPTON, Southampton (GB)

(72) Inventors: Franchesca D Houghton, Southampton (GB); Rahul S Tare, Southampton (GB); Lauren A Griffith, Southampton (GB)

(73) Assignee: University of Southampton, Southampton (GB)

( * ) Notice: Subject to any disclaimer, the term of this patent is extended or adjusted under 35 U.S.C. 154(b) by 830 days.

(21) Appl. No.: 17/429,130

(22) PCT Filed: Feb. 7, 2020

(86) PCT No.: PCT/GB2020/050285
§ 371 (c)(1),
(2) Date: Aug. 6, 2021

(87) PCT Pub. No.: WO2020/161502
PCT Pub. Date: Aug. 13, 2020

(65) Prior Publication Data
US 2022/0193143 A1 Jun. 23, 2022

(30) Foreign Application Priority Data

Feb. 8, 2019 (GB) ...................................... 1901827
Feb. 11, 2019 (GB) ...................................... 1901882

(51) Int. Cl.
*A61K 35/32* (2015.01)
*C12N 5/00* (2006.01)
*C12N 5/077* (2010.01)

(52) U.S. Cl.
CPC ............ *A61K 35/32* (2013.01); *C12N 5/0081* (2013.01); *C12N 5/0655* (2013.01); *C12N 2500/02* (2013.01); *C12N 2501/115* (2013.01); *C12N 2501/13* (2013.01); *C12N 2501/15* (2013.01); *C12N 2501/155* (2013.01); *C12N 2501/16* (2013.01); *C12N 2501/19* (2013.01); *C12N 2501/415* (2013.01); *C12N 2506/02* (2013.01); *C12N 2506/45* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 10,100,283 B2 * | 10/2018 | Tsumaki | A61K 35/32 |
| 2010/0166713 A1 * | 7/2010 | Dalton | C12N 5/0606 |
| | | | 435/363 |
| 2016/0251623 A1 * | 9/2016 | Tsumaki | A61P 19/08 |
| | | | 424/93.7 |
| 2019/0322987 A1 * | 10/2019 | Liu | C12N 5/0663 |

FOREIGN PATENT DOCUMENTS

WO 2012013969 2/2012

OTHER PUBLICATIONS

Pattappa et al. (2019) Int. J. Mol. Sci. 20: 484 (20 pages) (Year: 2019).*
Beane, et al. (2012) Annals of Biomedical Engineering, vol. 40, No. 10, pp. 2079-2097. (Year: 2012).*
Oldershaw et al. (2010) Nature Biotechnology vol. 28, No. 11: 1187-1195 (Year: 2010).*
Pattappa et al. (2019) Int. J. Mol. Sci. 20: 484 (28 pages) (Year: 2019).*
Castro-Vinuelas et al. (2018) European Cells and Materials vol. 36: pp. 96-109. (Year: 2018).*
Diekman et al. (2012) PNAS vol. 109, No. 47: 19172-19177. (Year: 2012).*
Hardingham et al. (2002) Arthritis Res. 4 (Suppl. 3): S63-S68. (Year: 2002).*
Passaretti et al. (2001) Tissue Engineering vol. 7, No. 6, 805-815. (Year: 2001).*
Shearier et al., "Physiologically Low Oxygen Enhances Biomolecule Production and Stemness of Mesenchymal Stem Cell Spheroids", Tissue Engineering: Part C, 2016, 22, pp. 360-369.
Oldershaw et al., "Directed differentiation of human embryonic stem cells toward chondrocytes", Nature Biotechnology, 2010, 28(11), pp. 1187-1196.
Fotia et al., "Hypoxia enhances proliferation and stemness of human adipose-derived mesenchymal stem cells", Cytotechnology, 2015, 67(6), pp. 1073-1084.

(Continued)

*Primary Examiner* — Russell G Fiebig
(74) *Attorney, Agent, or Firm* — Armstrong Teasdale LLP

(57) ABSTRACT

The invention relates to a method for producing cartilage from pluripotent stem cells (PSCs), the method comprising providing chondrocytes by: 1) providing pluripotent stem cells (PSCs); 2) inducing differentiation of the PSCs into a primitive streak/mesendoderm by culturing the PSCs in hypoxic conditions, in a (mesendodermic) culture media comprising: i) a Wingless/Integrated (WNT) family member, ii) an Activin family member, and iii) a Fibroblast Growth Factor (FGF) family member; 3) inducing differentiation of the primitive streak/mesendoderm into a mesoderm by culturing the primitive streak/mesendoderm in hypoxic conditions, in a (mesodermic) culture media comprising: i) a FGF family member, ii) a bone morphogenetic protein (BMP) family member, iii) Follistatin, and iv) a Neurotrophin (NT); and 4) inducing differentiation of the mesoderm into chondrocytes by culturing the mesoderm in hypoxic conditions, in a (chondroinductive) culture media comprising: i) a FGF family member, ii) a BMP family member, iii) a Neurotrophin, and iv) a Growth/Differentiation Factor (GDF) family member; and forming a pellet of the chondrocytes and culturing the pellet of the chondrocytes in a culture media under hypoxic conditions to produce the cartilage. The invention further relates to methods of chondrocyte production, synthetically produced cartilage, and use in therapy.

19 Claims, 26 Drawing Sheets

(56)  References Cited

OTHER PUBLICATIONS

Driessen et al., "Cellular reprogramming for clinical cartilage repair", Cell Biol Toxicol, 2017, 33(4), pp. 329-349.

Chen et al., "Chemically defined conditions for human iPSC derivation and culture", Nat Methods, 2011, 8(5), pp. 424-429.

Christensen et al., "GLUT3 and PKM2 regulate OCT4 expression and support the hypoxic culture of human embryonic stem cells", Scientific Reports, 2015, 5(17500), pp. 1-14.

Li et al, "Application of an acoustofluidic perfusion bioreactor for cartilage tissue engineering", Lab on a Chip, 2014, 14, pp. 4475-4485.

Tare et al., "Tissue engineering strategies for cartilage generation—Micromass and three dimensional cultures using human chondrocytes and a continuous cell line", Biochemical and Biophysical Research Communications, 2005, 333, pp. 609-621.

International Search Report and Written Opinion dated Apr. 20, 2020 for International Application No. PCT/GB2020/050285.

Ezashi et al., "Low O2 tensions and the prevention of differentiation of hES cells", Proc. Natl. Acad. Sci. U.S.A., 2005, 102(13), pp. 4783-4788.

Forristal et al., "Hypoxia inducible factors regulate pluripotency and proliferation in human embryonic stem cells cultured at reduced oxygen tensions", Reproduction, 2010, 139(1), pp. 85-97.

Oldershaw et al., "A chemically-defined protocol for generating chondrocytes from human embryonic stem cells", Protocol Exchange, 2010, https://protocolexchange.researchsquare.com/article/nprot-1898/v1, pp. 1-12.

Adkar et al., "Highly efficient chondrogenic differentiation of human iPSCs and purification via a reporter allele generated by CRISPR-Cas9 genome editing", bioRxiv, 2018, pp. 1-32.

Search Report dated Jun. 25, 2019, and issued in connection with British Patent Application No. GB1901827.4, pp. 1-5.

* cited by examiner

Low mag = 500 μm; High mag = 100 μm

A

B

Safranin O staining - Low mag = 500 µm; High mag = 100 µm 19 weeks

Safranin O staining – low mag = 500 μm; high mag = 100 μm

A

B

Low mag = 1000 μm; High mag = 100 μm

CARTILAGE TISSUE

CROSS-REFERENCE TO RELATED APPLICATIONS

This application is a U.S. National Phase Application of PCT/GB2020/050285, filed Feb. 7, 2020, which claims the benefit of priority to GB Application No. 1901827.4, filed Feb. 8, 2019, and GB Application No. 1901882.9, filed Feb. 11, 2019, the contents of which are hereby expressly incorporated by reference in their entirety.

The present invention relates to cartilage, particularly cartilage tissue that has been derived from pluripotent stem cells. The invention also relates to methods of preparing chondrocytes and cartilage tissue. The invention extends to methods of treatment, such as repairing or replacing damaged cartilage tissue in a subject.

Osteoarthritis (OA) is the most common form of arthritis in the western world and is predominantly characterised by a loss of hyaline articular cartilage. OA affects around 8.75 million individuals in the UK and 27 million individuals in the USA. Due to the limited ability of adult articular cartilage for self-repair, OA is a progressive, debilitating disease that severely compromises the quality of life in affected individuals. Around 60% of men and 70% of women over the age of 60 years develop OA and it is estimated that around 630 million individuals suffer from OA worldwide. The disease, therefore, poses a significant financial burden not only to the healthcare system, but also to the wider economy due to loss of productivity. The total cost of OA to the UK economy is estimated at 1-2.5% of Gross National Product (GNP) per year.

Currently, there are no pharmacological agents that promote comprehensive healing of articular cartilage defects. In an attempt to repair articular cartilage damage at an early stage, the patients' own articular cartilage cells (autologous chondrocyte implantation) and bone marrow-derived stem cells (bone marrow stimulation) have been used to repair the damaged cartilage site. However, there are a number of limitations associated with the use of these cell types, namely a) invasive surgeries are required to harvest the cells, b) limited number of cells can be harvested from the body, and c) the quality of the cartilage produced at the site of damage is inferior to native cartilage and often necessitates joint replacement surgeries.

Joint replacements of the knee and hip offer a new lease of life to patients plagued by severe late-stage OA. Although knee or hip replacement surgeries are effective for reducing pain and restoring joint function, these procedures are not without risks and not universally successful. Moreover, failure of the replacement joint is a significant recurring problem that can lead to patient discomfort and expensive revision surgery (costing £34,000 compared to £7000 for the initial joint replacement surgery) with outcomes less effective than the original joint replacement. Out of the 160,000 knee and hip replacements carried out in the UK each year, almost 13,000 procedures are revision surgeries to replace the patient's original implant.

Regenerative medicine approaches for the repair of articular cartilage defects have previously been focused on cell-based therapies (such as autologous chondrocyte implantation or bone marrow stimulation) and cell- and scaffold-based therapies, such as third-generation matrix associated autologous chondrocyte implantation.

For example, known interventions for functional restoration of chondral defects include reparative bone marrow stimulation techniques and restorative approaches such as autologous chondrocyte implantation (ACI). Although ACI has demonstrated promising clinical results, there are a number of limitations associated with this technique, namely a limited number of human articular chondrocytes (HACs) that can be harvested from the donor sites, associated donor site morbidity, de-differentiation of chondrocytes due to expansion in monolayer cultures and their limited lifespan in vitro.

Bone marrow-derived mesenchymal stem cells (MSCs) have attracted much attention due to their extended self-renewal potential and ability to differentiate into multiple stromal lineages including cartilage; invasive techniques are however required to obtain bone marrow samples or aspirates. Additionally, high variability in the chondrogenic differentiation potential of MSCs from different individuals, lack of immunoprivileged characteristics, and reports of inferior fibrocartilaginous repair tissue generation and hypertrophic differentiation of MSC derived chondrocytes, have limited the use of MSCs for cartilage regeneration.

The focus of regenerative medicine approaches for the repair of articular cartilage defects has now shifted towards 3-dimensional (3D) cartilage constructs. In comparison to the sub-optimal clinical outcomes of cell-based approaches currently used for functional restoration of articular cartilage lesions, application of tissue engineered, 3D hyaline-like cartilage grafts can potentially provide more consistent clinical results by filling the entirety of the defect and contributing to the formation of hyaline-like cartilaginous repair tissue that can integrate with the native articular cartilage. Inasmuch as scaffold-based approaches have been employed to bioengineer cartilage grafts with appropriate functional properties, scaffold-free approaches are emerging as promising elements of a clinical translational pathway for functional restoration of articular cartilage defects.

Human embryonic stem cells (hESCs) constitute a readily accessible population of self-renewing, pluripotent cells with perceived immunoprivileged characteristics, which provide an unlimited source of cells for regenerative medicine applications. For example, it has been shown that chondrogenic cells derived from human embryonic stem cells (hESCs), using a chemically defined culture system, promote cartilage repair when implanted in focal defects of nude rats. However, such known methods of producing/repairing cartilage tissue (using embryonic stem cell derived-chondrocytes) constitute a cell-based therapy of cartilage repair, which suffers from the drawbacks mentioned above.

There is, therefore, a need for an improved method of producing chondrocytes and cartilage tissue as well as an improved method of repairing damaged cartilage tissue.

Hence, according to a first aspect of the invention, there is provided a method for producing cartilage from pluripotent stem cells (PSCs), the method comprising providing chondrocytes by:

1) providing pluripotent stem cells (PSCs);
2) inducing differentiation of the PSCs into a primitive streak/mesendoderm by culturing the PSCs in hypoxic conditions, in a (mesendodermic) culture media comprising:
   i) a Wingless/Integrated (WNT) family member,
   ii) an Activin family member, and
   iii) a Fibroblast Growth Factor (FGF) family member;
3) inducing differentiation of the primitive streak/mesendoderm into a mesoderm by culturing the primitive streak/mesendoderm in hypoxic conditions, in a (mesodermic) culture media comprising:

i) a FGF family member, ii) a bone morphogenetic protein (BMP) family member, iii) Follistatin, and iv) a Neurotrophin (NT); and 4) inducing differentiation of the mesoderm into chondrocytes by culturing the mesoderm in hypoxic conditions, in a (chondroinductive) culture media comprising:

i) a FGF family member, ii) a BMP family member, iii) a Neurotrophin, and iv) a Growth/Differentiation Factor (GDF) family member; and forming a pellet of the chondrocytes and culturing the pellet of the chondrocytes in a culture media under hypoxic conditions to produce the cartilage.

According to a second aspect of the invention, there is provided a method for producing chondrocytes, the method comprising:

1) providing pluripotent stem cells (PSCs);

2) inducing differentiation of the PSCs into a primitive streak/mesendoderm by culturing the PSCs in hypoxic conditions, in a (mesendodermic) culture media comprising:

i) a Wingless/Integrated (WNT) family member, ii) an Activin family member, and iii) a Fibroblast Growth Factor (FGF) family member;

3) inducing differentiation of the primitive streak/mesendoderm into a mesoderm by culturing the primitive streak/mesendoderm in hypoxic conditions, in a (mesodermic) culture media comprising:

i) a FGF family member, ii) a bone morphogenetic protein (BMP) family member, iii) Follistatin, and iv) a Neurotrophin (NT); and 4) inducing differentiation of the mesoderm into chondrocytes by culturing the mesoderm in hypoxic conditions, in a (chondroinductive) culture media comprising:

i) a FGF family member, ii) a BMP family member, iii) a Neurotrophin, and iv) a Growth/Differentiation Factor (GDF) family member.

According to another aspect, there is provided a method for producing a primitive streak/mesendoderm, the method comprising:

1) providing pluripotent stem cells (PSCs); and 2) inducing differentiation of the PSCs into a primitive streak/mesendoderm by culturing the PSCs in hypoxic conditions, in a (mesendodermic) culture media comprising:

i) a WNT family member, ii) an Activin family member, and iii) a FGF family member.

According to another aspect, there is provided a method for producing a mesoderm, the method comprising:

1) providing a primitive streak/mesendoderm; and 2) inducing differentiation of the primitive streak/mesendoderm into a mesoderm by culturing the primitive streak/mesendoderm in hypoxic conditions, in a (mesodermic) culture media comprising:

i) an FGF family member, ii) a BMP family member:

iii) Follistatin, and iv) a Neurotrophin (NT).

The primitive streak/mesendoderm (of step (1)) may be a primitive streak/mesendoderm produced by the method according to the preceding aspect.

According to another aspect, there is provided a method for producing chondrocytes, the method comprising:

1) providing a mesoderm; and 2) inducing differentiation of the mesoderm into chondrocytes by culturing the mesoderm in a (chondroinductive) culture media comprising:

i) an FGF family member, ii) a BMP family member, iii) a Neurotrophin, and iv) a GDF family member.

The mesoderm (of step (1)) may be a mesoderm produced by the method according to the preceding aspect.

According to another aspect, there is a provided a method for producing a mesoderm, the method comprising:

1) providing pluripotent stem cells (PSCs);

2) inducing differentiation of the PSCs into a primitive streak/mesendoderm by culturing the PSCs in hypoxic conditions, in a (mesendodermic) culture media comprising:

i) a WNT family member, ii) an Activin family member, and iii) a Fibroblast Growth Factor (FGF) family member; and 3) inducing differentiation of the primitive streak/mesendoderm into a mesoderm by culturing the primitive streak/mesendoderm in hypoxic conditions, in a (mesoseodermic) culture media comprising:

i) an FGF family member, ii) a BMP family member, iii) Follistatin, and iv) a Neurotrophin (NT).

According to another aspect, there is provided a method for producing chondrocytes, the method comprising:

1) providing a primitive streak/mesendoderm;

2) inducing differentiation of the primitive streak/mesendoderm into a mesoderm by culturing the primitive streak/mesendoderm in a (mesodermic) culture media comprising:

i) an FGF family member, ii) a BMP family member, iii) Follistatin, iv) a Neurotrophin; and 3) inducing differentiation of the mesoderm into chondrocytes by culturing the mesoderm in a (chondroinductive) culture media comprising:

i) an FGF family member, ii) a BMP family member, iii) a Neurotrophin (NT), and iv) a Growth/Differentiation Factor (GDF) family member.

The primitive streak/mesendoderm (of step (1)) may be a primitive streak/mesendoderm produced by a method according to an earlier aspect.

The method according to the invention can be used to reproducibly produce healthy chondrocytes. It has been found that by culturing PSCs, such as embryonic stem cells (ESCs), under hypoxic conditions, their proliferative capacity and pluripotent characteristics are maintained (while they are in stage 0). However, culturing PSCs under hypoxic conditions also stimulates differentiation of ESCs into chondrocytes. In addition, chondrocytes produced by the method according to the invention can be used to produce healthy, non-necrotic 3D cartilage tissue that closely resembles native hyaline cartilage tissue.

In one embodiment, the chondroinductive culture media may further comprise a TGF-β subfamily member, such as TGF-β3. Surprisingly, the addition of a TGF-β subfamily member, such as TGF-β3, to the chondroinductive culture media provides a robust chondrogenic stimulus. Thus, the addition of a TGF-β subfamily member to the culture media significantly improves the reproducibility of the conversion of PSCs into healthy chondrocytes. The chondrocytes can subsequently be used to produce healthy, non-necrotic cartilage tissue by, for example, culturing them in vitro.

The method according to the invention may further comprise the step of culturing the chondrocytes as a pellet of chondrocytes in order to generate 3D cartilage tissue (i.e. a scaffold-free hyaline cartilage construct). Preferably, the chondrocytes are cultured as a pellet under hypoxic conditions. The media in which the chondrocytes are cultured may be referred to as a chondrogenic culture media. A (chondrogenic) culture media may be used to culture chondrocytes. A (chondrogenic) culture media may be used to culture a pellet of chondrocytes, such that the pellet differentiates into cartilage tissue.

The WNT family member may be selected from the group comprising/consisting of WNT1, WNT2, WNT2B, WNT3, WNT3A, WNT4, WNT5A, WNT6, WNT7A, WNT7B, WNT8A, WNT8B, WNT9A, WNT9B, WNT10A, WNT10B, WNT11 and WNT16. In one embodiment, the WNT family member is WNT3A. The WNT may be a human WNT, such as human WNT3A. In another embodiment, the WNT may be a mouse WNT, such as mouse WNT3A.

The Activin family member may be selected from the group comprising/consisting of Activin A, Activin B and Activin AB. In one embodiment, the Activin family member is Activin A. The Activin family member may be a human Activin family member, such as human Activin A.

The Fibroblast Growth Factor (FGF) family member may be selected from the group comprising/consisting of FGF1, FGF2, FGF3, FGF4, FGF5, FGF6, FGF7, FGF8, FGF9, FGF10, FGF11, FGF12, FGF13, FGF14, FGF15, FGF16, FGF17, FGF18, FGF19, FGF20, FGF21 and FGF22. Preferably, the FGF family member binds to an FGF receptor (FGFR). In one embodiment, the FGF family member is FGF2. The FGF family member may be a human family member, such as hFGF2.

The Bone Morphogenic Protein (BMP) family member may be selected from the group comprising/consisting of BMP1, BMP2, BMP3, BMP4, BMP5, BMP6, BMP7, BMP8a, BMP8b, BMP10, BMP11 and BMP15. In one embodiment, the BMP family member is BMP4. The BMP family member may be a human family member, such as human BMP4.

The neurotrophin (NT) may be selected from the group comprising/consisting of Nerve Growth Factor (NGF), Brain-derived neurotrophic factor (BDGF), Neurotrophin 3 (NT3), Neurotrophin 4 (NT4), Ciliary Neurotrophic Factor (CNTF) and the GDNF family of ligands (such as, glial cell line-derived neurotrophic factor (GDNF), Neurturin (NRTN), and/or persephin (PSPN)). In one embodiment, the Neurotrophin is NT4. The neurotrophin may be a human neurotrophin, such as human NT4.

The Growth/Differentiation Factor (GDF) family member selected from the group comprising/consisting of GDF1, GDF2, GDF3, GDF4, GDF5, GDF6, GDF7, GDF8, GDF9, GDF10, GDF11, GDF12, GDF13, GDF14 and GDF15. In one embodiment, the Growth/Differentiation Factor family member is GDF5. The Growth/Differentiation Factor (GDF) family member may be a human GDF family member, such as human GDF5.

The Transforming Growth Factor-β (TGF-β) subfamily member may be one that it is capable of binding to a TGF-β receptor, such as a TGF-β subfamily member selected from the group comprising/consisting of TGF-β1, TGF-β2, TGF-β3 and TGF-β4. In one embodiment, the TGF-β subfamily member is TGF-β3. The addition of a TGF-β subfamily member, particularly TGB-β3, to the culture media enhanced the chondrogenic stimuli and increased the reproducibility of cartilage tissue formation. The TGF-β subfamily member may be a human TGF-β subfamily member, such as human TGF-β3.

The mesendodermic culture media of step (2) of the first or second aspect (i.e. the step of inducing differentiation of the PSCs into a primitive streak/mesendoderm) preferably comprises WNT3A, Activin A and FGF2; the culture media of step (3) (i.e. the step of inducing differentiation of the primitive streak/mesendoderm into a mesoderm) comprises FGF2, Follistatin, BMP4 and NT4; and the culture media of step (4) (i.e. the step of inducing differentiation of the mesoderm into chondrocytes) comprises FGF2, BMP4, NT4 and GDF5. Step (4) of the method according to the first or second aspect may further comprise a TGF-β family member, preferably TGF-β3.

Similarly, the culture media of the method according to the other preceding aspects of the invention (i.e. excluding the method according to the first or second aspect) comprise, where appropriate, the same preferred growth factors as those mentioned above in relation to the first or second aspect. Thus, the culture media of the step of inducing differentiation of the primitive streak/mesendoderm into a mesoderm preferably comprises WNT3A, Activin A and FGF2. The culture media of the step of inducing differentiation of the primitive streak/mesendoderm into a mesoderm preferably comprises FGF2, Follistatin, BMP4 and NT4. The culture media of step of inducing differentiation of the mesoderm into chondrocytes preferably comprises FGF2, BMP4, NT4 and GDF5.

Preferably, step (2) of the method according to the first or second aspect (i.e. the step of inducing differentiation of the PSCs into a primitive streak/mesendoderm) comprises culturing the PSCs for 4 days, such that a substantial amount of the PSCs have differentiated into a primitive streak/mesendoderm, step (3) of the method according to the first or second aspect (i.e. the step of inducing differentiation of a primitive streak/mesendoderm into a mesoderm) comprises culturing the primitive streak/mesendoderm for 5 days, such that a substantial amount of the cells have differentiated into a mesoderm, and step (4) of the method according to the first or second aspect (i.e. the step of inducing differentiation of a mesoderm into chondrocytes) comprises culturing the mesoderm for 5 days, such that a substantial amount of the cells have differentiated into chondrocytes. Similarly, the culture media of the method according to the other aspects of the invention comprises, where appropriate, culturing the relevant cells such that a substantial amount of the cells differentiate.

The Step of Providing Pluripotent Stem Cells (PSCs)

The PSCs may be from a primary cell culture, a secondary cell culture or a cell line. The PSCs may be human (i.e. hPSCs), equine, horse, simian, monkey, canine, or feline. The PSCs may be induced pluripotent stem cells (iPSCs). Preferably, the method according to the invention does not comprise destroying an embryo, particularly a human embryo. The method according to the invention may comprise parthenote-derived pluripotent stem cells.

The PSCs may be embryonic stem cells (ESCs) or induced pluripotent stem cells (iPSCs). Most preferably, the ESCs or iPSCs are human (i.e. hESCs or hiPSCs). The hESCs may be HUES7 hESC cell line, or hESCs from other hESC cell lines. The hiPSCs may be NIBSC-8 hiPSC cell line, or hiPSCs from other hiPSC cell lines.

PSCs may be cultured until they reach 50% to 80% confluence, most preferably 70% confluence. After reaching the relevant confluence, the cells may be re-plated. The stem cells may be cultured with feeder cells or under feeder-free conditions.

In one embodiment, the PSCs, such as hESCs, are cultured in hypoxic conditions prior to initiating differentiation. In one embodiment, the PSCs, such as hESCs, are cultured for at least 1 to 3 passages prior to initiating differentiation. In one embodiment, the PSCs, such as hESCs, are cultured for at least 2 or 3 passages prior to initiating differentiation. For example, the PSCs may be cultured in about 5% Oxygen, 5% $CO_2$ and balanced nitrogen for at least 3 passages prior to differentiation. Preferably PSCs are cultured in a humidified environment. Prior to culturing the PSCs in a hypoxic environment (which may occur for at least 1, 2 or 3 passages), the PSCs may be cultured in atmospheric levels of oxygen and $CO_2$, such as 20% oxygen and 4-7% $CO_2$ (preferably 5% $CO_2$). In another embodiment, prior to initiating differentiation, the PSCs are cultured in atmospheric levels of oxygen and $CO_2$, such as 18-22% oxygen and 4-7% $CO_2$ (preferably 20% oxygen and 5% $CO_2$).

The PSCs may be cultured on a substrate, such as a protein substrate, or protein-coated substrate. The substrate for culture of PSCs may comprise fibronectin, vitronectin or a gelatinous protein mixture secreted by Engelbreth-Holm-Swarm (EHS) mouse sarcoma cells (Matrigel). In one embodiment, the substrate for culture of PSCs may comprise or consist of vitronectin. In another embodiment, the substrate for culture of PSCs may comprise or consist of fibronectin. In another embodiment, the substrate for culture of PSCs may comprise or consist of Matrigel. The cells may be provided in a γ-irradiated mouse embryonic fibroblast-conditioned media. The media may comprise Knockout DMEM supplemented with knockout serum replacement, L-glutamax, bFGF, penicillin/streptomycin, non-essential amino acids and β-mercaptoethanol. A number of standard PSC appropriate media are available to the skilled person for the culture of PSCs. For example PSC media may comprise one of mTeSR™ media, Essential 8™ media (https://beta-static.fishersci.com/content/dam/fishersci/en_EU/promo-tions/12419_Cell_Culture/PDFs/Scale-up/COL21321_Gibco_Essential_8_Media_Brochure_Global.pdf), PluriSTEM® media, and StemFlex™ media, or a medium comprising the components thereof. Suitable medium and conditions are also described by Chen et al (Nat Methods. 2011 May; 8(5): 424-429. doi:10.1038/nmeth.1593), which is herein incorporated by reference.

The step of providing PSCs may comprise providing the PSCs, such as ESCs, in culture. The PSCs may be PSCs that have (already) been obtained from a subject.

The determination that a cell is a PSC may comprise detection of a cellular biomarker. A cellular biomarker of a PSC may be one or more of the cell markers selected from the group comprising/consisting of OCT4, SOX2, NANOG, TRA-1-60, TRA-1-81, SSEA3, SSEA4 and ALP.

The determination that a cell is a hESC may comprise detection of a cellular biomarker. A cellular biomarker of a hESC may be one or more of the cell markers selected from the group comprising/consisting of: OCT4, SOX2 and NANOG, TRA-1-60, TRA-1-81, SSEA3, SSEA4 and ALP.

The determination that a cell is a hiPSC may comprise detection of a cellular biomarker. A cellular biomarker of a hiPSC may be one or more of the cell markers selected from the group comprising/consisting of: OCT4, SOX2 and NANOG, TRA-1-60, TRA-1-81, SSEA3, SSEA4 and ALP.

The Step of Inducing Differentiation of PSCs into a Primitive Streak/Mesendoderm The primitive streak/mesendoderm is a precursor to the mesoderm stage of chondrocyte differentiation. The step of inducing differentiation of PSCs into a primitive streak/mesendoderm may comprise culturing the PSCs in a (mesendodermic) culture media over a period of time sufficient to form primitive streak/mesendoderm.

The determination that the primitive streak/mesendoderm has been formed may comprise detection of a cellular biomarker. A cellular biomarker of a primitive streak/mesendoderm may be selected from the group comprising or consisting of: CDH1 (E-cadherin), GSC2 (Goosecoid), T (Brachyury), FOXA2 (hepatocyte nuclear factor 3β) and MIXL (mix-Like) homeobox protein 1.

The primitive streak/mesendoderm may be considered to have formed (i.e. for moving onto the next step) when a substantial amount of the cells have differentiated. The primitive streak/mesendoderm may be considered to have formed when at least 60% of the cells are primitive streak/mesendoderm cells. In another embodiment, the primitive streak/mesendoderm may be considered to have formed when at least 70% of the cells are primitive streak/mesendoderm cells. In another embodiment, the primitive streak/mesendoderm may be considered to have formed when at least 80% of the cells are primitive streak/mesendoderm cells. In another embodiment, the primitive streak/mesendoderm may be considered to have formed when at least 85% of the cells are primitive streak/mesendoderm cells.

The method according to the invention may comprise culturing the PSCs in a (mesendodermic) culture media for 2 to 6 days, preferably 3 to 5 days, most preferably 4 days.

Preferably, the (mesendodermic) culture media of the step of inducing differentiation of PSCs into a primitive streak/mesendoderm comprises WNT3A, Activin A and FGF2.

Following the step of inducing differentiation of PSCs into primitive streak/mesendoderm, is the step of inducing differentiation of primitive streak/mesendoderm into a mesoderm. The culture media used in the step of inducing differentiation of PSCs into a primitive streak/mesendoderm may be replaced with the culture media used in the step of inducing differentiation of a primitive streak/mesendoderm into a mesoderm. Replacement of the culture media used in the step of inducing differentiation of PSCs into a primitive streak/mesendoderm may comprise aspirating and discarding the media.

The Step of Inducing Differentiation of a Primitive Streak/Mesendoderm into a Mesoderm The step of inducing differentiation of a primitive streak/mesendoderm into a mesoderm may comprise culturing the primitive streak/mesendoderm in a (mesodermic) culture medium over a period of time sufficient to form a mesoderm.

The determination that a mesoderm has been formed may comprise detection of a cellular biomarker. A cellular biomarker of a mesoderm may be selected from the group comprising or consisting of: CXCR4, (C-X-C chemokine receptor type 4), T (brachyury), KDR (Vascular endothelial growth factor receptor 2), TBX6 (T box transcription factor 6), CAD11 (Cadherin 11), PDGFRA (Platelet Derived Growth Factor Receptor Alpha) and PDGFRB (Platelet Derived Growth Factor Receptor Beta).

The mesoderm may be considered formed (i.e. for moving onto the next step) when a substantial amount of the cells have differentiated. The mesoderm may have been formed when at least 60% of the cells are mesoderm cells. In another embodiment, the mesoderm may be considered to have formed when at least 70% of the cells are mesoderm cells. In another embodiment, the mesoderm may be considered to have formed when at least 80% of the cells are mesoderm cells. In another embodiment, the mesoderm may be considered to have formed when at least 85% of the cells are mesoderm cells.

The method according to the invention may comprise culturing the primitive streak/mesendoderm in a (mesodermic) culture media for 3 to 7 days, preferably 4 to 6 days, most preferably 5 days.

Preferably, the (mesodermic) culture media of the step of inducing differentiation of a primitive streak/mesendoderm into a mesoderm comprises FGF2, Follistatin, BMP4 and NT4.

Following the step of inducing differentiation of primitive streak/mesendoderm into a mesoderm, is the step of inducing differentiation of a mesoderm into chondrocytes. The culture media used in the step of inducing differentiation of primitive streak/mesendoderm into mesoderm may be replaced with the culture media used in the step of inducing differentiation of mesoderm into chondrocytes. Replacement of the culture media used in the step of inducing differentiation of a primitive streak/mesendoderm into mesoderm may comprise aspirating and discarding the media.

The Step of Inducing Differentiation of a Mesoderm into Chondrocytes

Chondrocytes are cells responsible for the production of cartilage. The step of inducing differentiation of mesoderm into chondrocytes may comprise culturing mesoderm in a (chondroinductive) culture medium over a period of time sufficient to form chondrocytes.

The determination that chondrocytes have been formed may comprise detection of a cellular biomarker. A cellular biomarker of chondrocytes may be selected from the group comprising or consisting of: SOX9, (Sex determining region Y-Box 9), COL2A1 (Type II collagen), SOX6 (Sex determining region Y-Box 6), SOX5 (Sex determining region Y-Box 5) Aggrecan and CD44. The chondrocytes may not express one or more of OCT4, NANOG, and SOX2.

The chondrocytes may be considered to have formed (i.e. for moving onto the next step) when a substantial amount of the cells have differentiated. The chondrocytes may be considered to have formed when at least 60% of the cells are chondrocytes. In another embodiment, the chondrocytes may be considered to have formed when at least 70% of the cells are chondrocytes. In another embodiment, the chondrocytes may be considered to have formed when at least 80% of the cells are chondrocytes. In another embodiment, the chondrocytes may be considered to have formed when at least 85% of the cells are chondrocytes. In another embodiment, the chondrocytes may be considered to have formed when at least 90% of the cells are chondrocytes.

The step of inducing differentiation of a mesoderm into chondrocytes may comprise culturing the mesoderm in a (chondroinductive) culture media for about 5 days, about 6 days, about 7 days, about 8 days, about 9 days, about 10 days or about 11 days in a (chondroinductive) culture media. The method may comprise culturing the mesoderm in a (chondroinductive) media for 4 to 6 days, 4 to 7 days, 4 to 8 days, 4 to 9 days, 4 to 10 days or 4 to 11 days. Most preferably, the method comprises culturing the mesoderm for 5 days in in a (chondroinductive) culture media.

In one embodiment, the method may further include a step to derive a homogeneous population of the chondrocytes by filtering or selecting for the chondrocytes produced according to the method. The step of deriving a homogeneous population of the chondrocytes may be prior to forming a pellet and/or cartilage. In one embodiment, pluripotent stem cells (PSCs) may be removed from the chondrocytes to provide a homogenous population of the chondrocytes. In one embodiment, cells expressing markers of PSCs may be removed from the chondrocytes to provide a homogenous population of the chondrocytes. In one embodiment, cells expressing one, two, or all, of OCT4, NANOG, and SOX2, may be removed from the chondrocytes to provide a homogenous population of the chondrocytes.

The chondrocytes may be selected for by culturing the chondrocytes under conditions that retain chondrocytes and do not retain PSCs. For example, the chondrocytes may be selected for by passaging the chondrocytes onto a selective membrane or surface, such as tissue culture plastic. The selective membrane or surface may allow the adherence of the chondrocytes and discourage the adherence of pluripotent stem cells.

In one embodiment, the chondrocytes may be selected for by passaging the chondrocytes onto tissue culture plastic and with fresh culture medium, such as chondroinductive culture medium, and culturing the chondrocytes under hypoxic conditions for at least 1 day (i.e. at least 24 hours). Culturing the passaged chondrocytes on tissue culture plastic under hypoxic conditions may be for about 3 days, or more. In another embodiment, culturing the passaged chondrocytes on tissue culture plastic under hypoxic conditions may be for about 2-10 days. In another embodiment, culturing the passaged chondrocytes on tissue culture plastic under hypoxic conditions may be for about 3-10 days. In another embodiment, culturing the passaged chondrocytes on tissue culture plastic under hypoxic conditions may be for about 2-6 days. In another embodiment, culturing the passaged chondrocytes on tissue culture plastic under hypoxic conditions may be for about 3-6 days. In another embodiment, further culturing the passaged chondrocytes on tissue culture plastic under hypoxic conditions may be for about 3-4 days. In another embodiment, culturing the passaged chondrocytes on tissue culture plastic under hypoxic conditions may be for a period until OCT4 expression is substantially undetectable. The period may be until one, two or all of OCT4, NANOG, and SOX2 expression is undetectable. The skilled person may monitor one, two or all of OCT4, NANOG, and SOX2 expression to determine the period for further culturing the passaged chondrocytes under hypoxic conditions (i.e. until at least when OCT4 expression is substantially undetectable). The detection of expression may comprise the use of immunocytochemistry, western blot, or RT-PCR.

The passaging of the chondrocytes into fresh culture medium, such as chondroinductive culture medium, may be passaging the chondrocytes onto plasticware, such as tissue culture plastic.

Therefore, in one embodiment, the method may further comprise the step of passaging of the chondrocytes into fresh culture medium, such as chondroinductive culture medium, onto tissue culture plastic for about 3 days.

The presence of OCT4, NANOG, and/or SOX2 expressing cells in the chondrocytes can potentially lead to safety concerns, where implanted cartilage comprising pluripotent cells could be a tumour risk for a patient. Advantageously, the present invention has found that the produced chondrocytes can adhere to substrates such as plasticware for continued culture, where PSCs (e.g. cells expressing pluripotency markers OCT4, NANOG, and/or SOX2) cannot. This allows a homologous culture of the chondrocytes to be provided.

In another embodiment, the chondrocytes may be filtered/selected for by cell sorting, for example by FACS (fluorescence activated cell sorting) or MACS (magnetic activated cell sorting). PSCs (cells expressing pluripotent stem cell markers) may be filtered/selected out by cell sorting, for example by FACS or MACS.

In one embodiment, the (chondroinductive) culture media of the step of inducing differentiation of a mesoderm into chondrocytes and/or deriving a homogeneous population of chondrocytes comprises FGF2, BMP4, NT4 and GDF5. Preferably, the (chondroinductive) culture media of the step of inducing differentiation of a mesoderm into chondrocytes and/or deriving a homogeneous population of chondrocytes comprises FGF2, BMP4, NT4 and GDF5, and TGF-β3.

The (chondroinductive) culture media may comprise a TGF-β subfamily member. The TGF-β subfamily member, such as TGF-β3, may be provided at a concentration of about 10 ng/ml. The TGF-β subfamily member, such as TGF-β3, may be provided at a concentration of between about 5 ng/ml and about 15 ng/ml. The TGF-β subfamily member, such as TGF-β3, may be provided at a concentration between about 8 ng/ml and about 12 ng/ml.

According to another aspect, there is provided a method of producing cartilage tissue comprising chondrocytes, the method comprising culturing a pellet of chondrocytes in a culture media under hypoxic conditions.

According to another aspect, there is provided a method of producing cartilage tissue comprising chondrocytes, the method comprising culturing a pellet of chondrocytes on a substrate under hypoxic conditions.

The method of producing cartilage tissue may comprise culturing a pellet of chondrocytes in a (chondrogenic) culture media.

The substrate may comprise cartilage. The cartilage may be synthetically produced, for example according to the method of the invention, or may be a natural cartilage extract. The substrate may be a cartilage extract or a porous membrane, such as a porous biomembrane. The porous membrane may be porous to gas, to liquid, or porous to gas and liquid. The porous membrane may comprise polytetrafluoroethylene (PTFE), polycarbonate, polyester or polyethylene terephthalate (PET).

Preferably, the cartilage, such as the cartilage extract, has a partial thickness defect, which defines a cavity or indentation in the extract for receiving a pellet of chondrocytes. In one embodiment, the substrate, such as cartilage, comprises a cavity or indent for receiving a pellet of chondrocytes.

Surprisingly, culturing the pellet of chondrocytes on a substrate results in significant and prolific growth of the pellet to produce large amounts of cartilage tissue.

The cartilage tissue of the invention is 3D and resembles that of native cartilage tissue, specifically, hyaline cartilage. Advantageously, therefore, the cartilage tissue may be analysed (in vitro) prior to implantation in vivo to determine if it is suitable for use.

The method of producing cartilage tissue may further comprise culturing the chondrocytes, which have been produced by any one of the preceding aspects, as a pellet of cells, such that they produce a 3D cartilage tissue.

The (chondroinductive) culture media used in the step of inducing differentiation of a mesoderm into chondrocytes may be replaced with the (chondrogenic) culture media used for the culture of the pellet of chondrocytes. Replacement of the (chondroinductive) culture media may comprise aspirating and discarding the (chondroinductive) media used to induce differentiation of the mesoderm into chondrocytes. Prior to the addition of the (chondrogenic) culture media used for the culture of the pellet of chondrocytes, the chondrocytes may be washed. The chondrocytes may be washed in chondroinductive media, chondrogenic culture media or phosphate-buffered saline (PBS).

Preferably, the chondrogenic culture media used for culture of the pellet of chondrocytes comprises a TGF-β subfamily member, such as TGF-β3. The chondrogenic culture media may further comprise dexamethasone, ascorbate-2-phosphate, L-proline and ITS (insulin, transferrin, selenium). In one embodiment, the chondrogenic culture media is supplemented with about 10 ng/ml TGF-β3, about 10 nM dexamethasone, about 100 μM ascorbate-2-phosphate, about 0.35 mM L-Proline and about a 1×ITS supplement, such as 10 μg/ml insulin, 5.5 μg/ml transferrin, 5 ng/ml sodium selenite. The culture media may be supplemented with 8 to 12 ng/ml TGF-β3, 8 to 10 nM dexamethasone, 80 to 100 μM ascorbate-2-phosphate, 0.3 to 0.4 mM L-Proline and/or a 1×ITS supplement.

The inventors have found that the longer that a pellet of chondrocytes is cultured the larger the cartilage tissue will become. However, if a pellet of chondrocytes is cultured for less than 3 weeks it will not form robust cartilage. Therefore, the pellet of chondrocytes may be cultured for at least 3 weeks, at least 4 weeks, at least 6 weeks, at least 8 weeks, at least 10 weeks, at least 12 weeks, at least 14 weeks, at least 16 weeks, at least 18 weeks, at least 19 weeks or at least 26 weeks. Preferably, the pellet of chondrocytes is cultured for 19 weeks.

A pellet of chondrocytes can refer to a 3D aggregate of chondrocytes or a 3D aggregate of chondrocytes and cartilage. A pellet of chondrocytes does not refer to a 2D aggregate/layer of cells or chondrocytes that are in a suspension. A pellet of chondrocytes may be produced by aggregating the chondrocytes together. Aggregation of the cells together may be achieved, for example, by centrifugation of a suspension of chondrocytes in a vessel for cell culture. The vessel for cell culture may comprise a pointed base. The vessel for example, may be a universal tube. The pellet of chondrocytes may be cultured in a vessel for cell culture, with a pointed base, such as a universal tube, an Eppendorf, Falcon tube, or any other plasticware with a pointed base.

The chondrocytes referred to herein may be chondrocytes produced by the method according to the invention.

According to another aspect of the invention, there is provided a cartilage tissue comprising chondrocytes at a mean average density of approximately 5-20 chondrocytes/μm².

The cartilage tissue may be synthetic cartilage tissue, for example the cartilage tissue may be synthetically produced, or otherwise produced in vitro. The cartilage tissue may be ex vivo. The cartilage tissue may not comprise or consist of natural cartilage extract.

The inventors have generated a tissue-engineered product in the form of cartilage tissue that has been derived (or cultured) from PSCs, such as ESCs. The cartilage tissue may be used, in a method of treatment according to the invention, as a tissue-based therapy for restoring and/or repairing cartilage, particularly, articular cartilage. This will improve long term patient outcome and overall wellbeing, and reduce the need for joint replacement surgeries.

According to another aspect of the present invention, there is provided a method of repairing or replacing damaged cartilage tissue in a subject, the method comprising implanting in vitro derived cartilage tissue into the subject, wherein the in vitro derived cartilage tissue has been produced by the method of the invention herein.

The implantation may be within a defect of the subject's natural/native cartilage. In another embodiment, the implantation may be within a surgically prepared excision of the subject's natural/native cartilage.

According to another aspect of the invention, there is provided a cartilage tissue produced by the method according to the invention herein for use in therapy/as a medicament.

The cartilage tissue produced by the method according to the invention herein may be for use as an implant, such as a therapeutic implant.

The therapy may comprise treating, restoring or repairing damaged cartilage tissue, or treating or preventing a cartilage disorder.

The damaged cartilage may be articular cartilage tissue or growth plate cartilage. The damage to the cartilage tissue may be caused by a cartilage disorder. The cartilage disorder may be arthritis, osteoarthritis, chondritis, a partial thickness defect of native cartilage, or a full thickness defect of native cartilage.

Chondrocytes produced by culturing PSCs, such as ESCs or iPSCs, using the method according to the invention may comprise one or more of the cell biomarkers selected from the group comprising/consisting of: SOX9 and COL2A1, SOX6 (Sex determining region Y-Box 6), SOX5 (Sex determining region Y-Box 5), Aggrecan and CD44.

Chondrocytes produced by culturing PSCs using the method according to the invention may not comprise one or more of the cell biomarkers selected from the group comprising OCT4, NANOG, and SOX2.

Cartilage tissue produced by the method according to the invention may comprise one or more of the cell biomarkers selected from the group comprising/consisting of: Type II collagen, aggrecan, Type IX collagen, Type XI collagen, chondroitin sulphate and hyaluronic acid. Type I collagen is preferably absent.

Cartilage tissue produced by the method according to the invention may be hyaline cartilage tissue. The cartilage tissue may be cartilage tissue produced by the method according to the invention. Cartilage tissue according to the invention may further comprise an extracellular matrix (ECM).

The PSCs according to any one of the preceding aspects may be human embryonic stem cells (hESCs). Preferably, the ESCs are hESCs. The hESCs may be a HUES7 hESC cell line, a SHEF3 cell line or a H1 cell line. The skilled person will recognise that other hESC cell lines are available and may be used. If the ESCs are used in therapy (such as by treating, repairing, restoring, or replacing damaged cartilage tissue, or preventing a cartilage disorder in a subject), they may be autologous or heterologous. Preferably, the species of the (autologous) PSCs matches the species of the subject to be treated and/or matches the species of the damaged cartilage tissue. Most preferably, the PSCs are autologous (i.e. iPSCs).

"Hypoxic conditions" as referred to herein can refer to an environment with a low oxygen content. A low oxygen content may be an environment in which the oxygen content is 1% or less, 2% or less, 3% or less, 4% or less, 5% or less, 6% or less, 7% or less, 8% or less, 9% or less, or 10% or less. Preferably, the oxygen content is 6% or less, 5% or less or 4% or less. The oxygen content may be 1% to 10%, 2% to 9%, 3% to 8% or 4% to 7%. Preferably, the oxygen content is 3 to 8% or 4 to 7%. In one embodiment, the oxygen content is 5% or less. Most preferably, the oxygen content is 5%.

"Culture" or "culturing" as referred to herein refers to maintaining tissue or cells in conditions suitable for growth, such as in culture media at 37° C. Conditions suitable for growth can refer to an environment in which the $CO_2$ content is low (i.e. has a low $CO_2$ content). A low $CO_2$ content may be 1% or less, 2% or less, 3% or less, 4% or less, 5% or less, 6% or less, 7% or less, 8% or less, 9% or less, or 10% or less. In another embodiment, a low $CO_2$ content may be 15% or less. Preferably, the $CO_2$ content is 6% or less, 5% or less or 4% or less. The $CO_2$ content may be 1% to 10%, 2% to 9%, 3% to 8% or 4% to 7%. Preferably, the $CO_2$ content is 3 to 8% or 4 to 7%. In one embodiment, the $CO_2$ content is 5% or less. Most preferably, the $CO_2$ content is 5%. In another embodiment, a low $CO_2$ content may be 15% or less and the $O_2$ content may be about 3-8%, or up to 5%. In another embodiment, a low $CO_2$ content may be 10% or less and the $O_2$ content may be about 3-8%, or up to 5%. In another embodiment, a low $CO_2$ content may be 15% or less and the $O_2$ content may be about 5%. In another embodiment, a low $CO_2$ content may be 10% or less and the $O_2$ content may be about 5%.

"Mesendodermic culture media" can refer to a culture media that promotes differentiation of the ESCs into primitive streak/mesendoderm. Therefore, a mesendodermic media may be the culture media of, for example, step (2) of the method of the first or second aspect. The "mesendodermic culture media" may alternatively be referred to as a "culture media". The term "mesendodermic" is non-limiting and has been used for descriptive purposes only.

"Mesodermic culture media" can refer to a culture media that promotes differentiation of primitive streak/mesendoderm into a mesoderm. Therefore, a mesodermic media may be the culture media of, for example, step (3) of the method of the first or second aspect. The "mesodermic culture media" may alternatively be referred to as a "culture media". The term "mesodermic" is non-limiting and has been used for descriptive purposes only.

"Chondroinductive culture media" can refer to a culture media that promotes differentiation of a mesoderm into chondrocytes. Therefore, a chondroinductive media may be the culture media of, for example, step (4) of the method of the first or second aspect. The "chondroinductive culture media" may alternatively be referred to as a "culture media". The term "chondroinductive" culture media is non-limiting and has been used for descriptive purposes only.

"Chondrogenic culture media" can refer to culture media used to culture chondrocytes or culture a pellet of chondrocytes, such that the pellet of chondrocytes differentiates into a cartilage pellet or cartilage tissue. The "chondrogenic culture media" may alternatively be referred to as a "culture media". The term "chondrogenic" culture media is non-limiting and has been used for descriptive purposes only.

"A porous biomembrane" can refer to a biological membrane, which is porous to gases and/or liquids. It can also refer to tissue that is non-toxic to a mammalian cell, body or tissue (in the quantity it is intended to be used).

"A primary cell culture" can refer to cells that have been obtained directly from an animal or plant, or an animal or plant tissue, dissociated (for example, using an enzyme or a mechanical measure) and then placed into cell culture.

"A secondary cell culture" can refer to cells that have been obtained from a cell culture, such as primary cell culture or a cell line.

The term "substantial amount" can refer to approximately at least 40%, approximately at least 50%, approximately at least 60%, approximately at least 70%, approximately at least 80% or approximately at least 90% of the cells referred to herein. For example, approximately at least 60% of the cells in a culture of PSCs are converted into primitive streak/mesendoderm (step (2) of the first or second aspect).

"Autologous" can refer to cells or tissue obtained from the same individual. Thus, for example, the subject may be the donor of adult somatic cells and the recipient of the chondrocytes of the invention or the subject's tissue may be the recipient of the chondrocytes. The adult somatic cells may be reprogrammed such that they form iPSCs.

"Heterologous" can refer to cells or tissue obtained from a different subject but from the same species of the subject whose tissue is to be repaired or replaced, or it can refer to cells or tissue obtained from a different species.

All of the features described herein (including any accompanying claims, abstract and drawings), and/or all of the steps of any method or process so disclosed, may be combined with any of the above aspects in any combination, unless stated otherwise with reference to a specific combinations, for example, combinations where at least some of such features and/or steps are mutually exclusive.

For a better understanding of the invention, and to show how embodiments of the same may be carried into effect, reference will now be made, by way of example only, to the accompanying drawings, in which:—

FIG. 2 shows the protocol and growth factors used to induce differentiation of hESCs into primitive streak/mesendoderm, followed by mesoderm and then chondrocytes.

Figure 1:
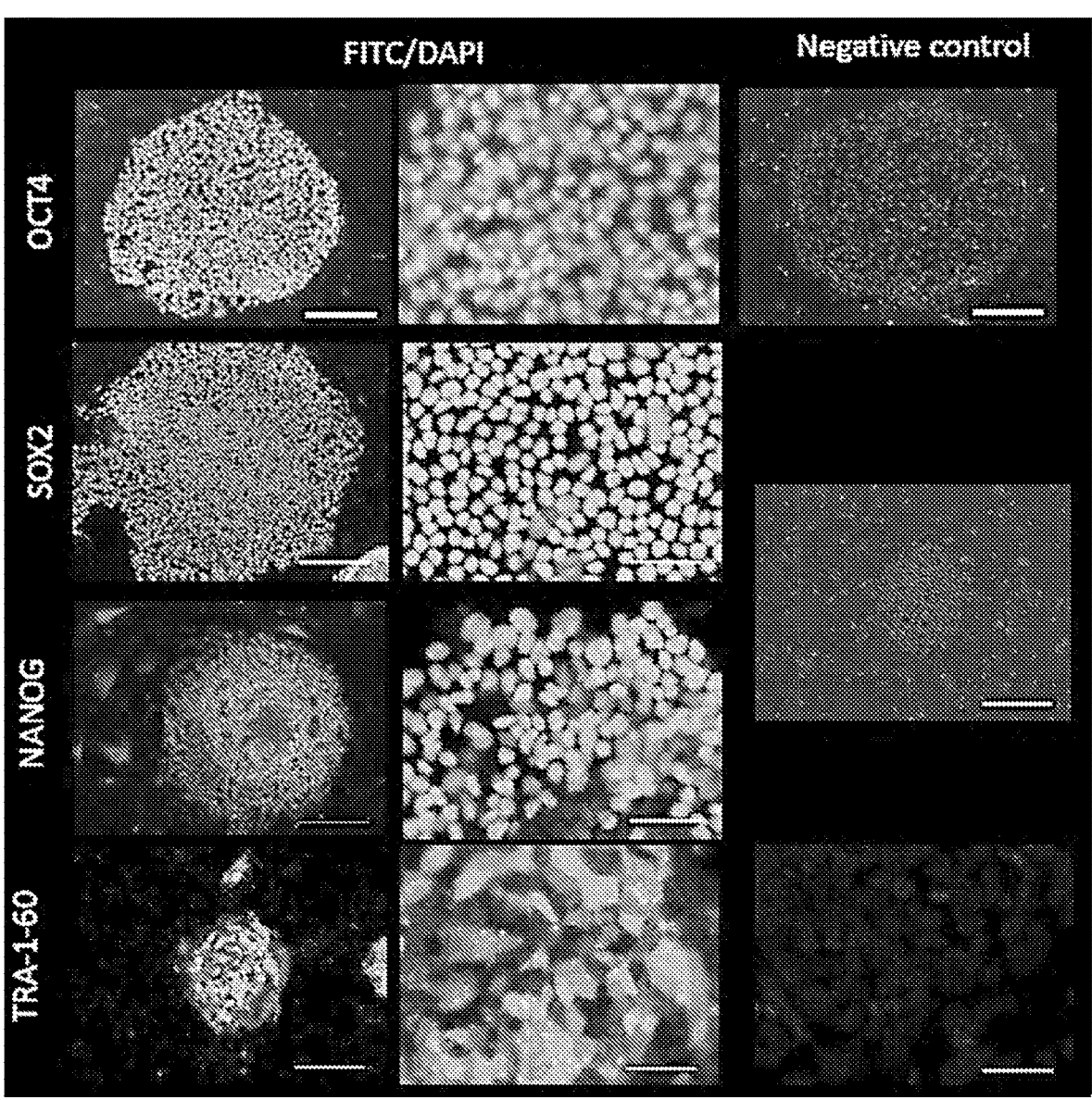
FIG. 1 shows immunocytochemistry of hESCs demonstrating OCT4, SOX2, NANOG and TRA-1-60 expression.
Figure 7:
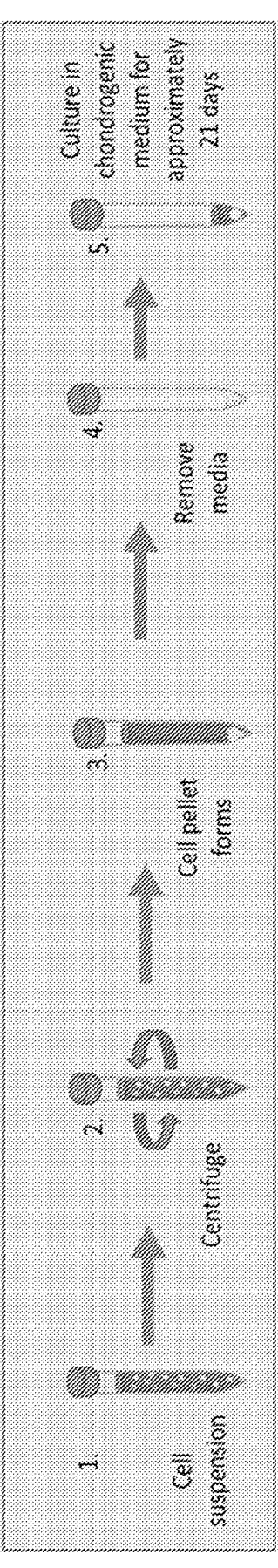

FIG. 6 shows bar charts which quantify the change in expression of OCT4, SOX2, NANOG, SOX9 and Type II collagen in hESCs (at stage 0) and hESC-derived chondrocytes (stage 3). For OCT4, SOX2 and NANOG, data were normalised to β-ACTIN and stage 3 was compared to stage 0, which was set to 1. For SOX9 and Type II collagen, data were normalised to β-ACTIN and stage 0 was compared to stage 3, which was set to 1. Values represent mean±SD. Asterisks indicate a statistically significant difference. *$p \leq 0.05$, $p \leq 0.01$, *$p \leq 0.001$ (Student's t-test);

FIG. 7 is a schematic of the protocol used for pellet culture of hESC-derived chondrocytes.

Figure 8:
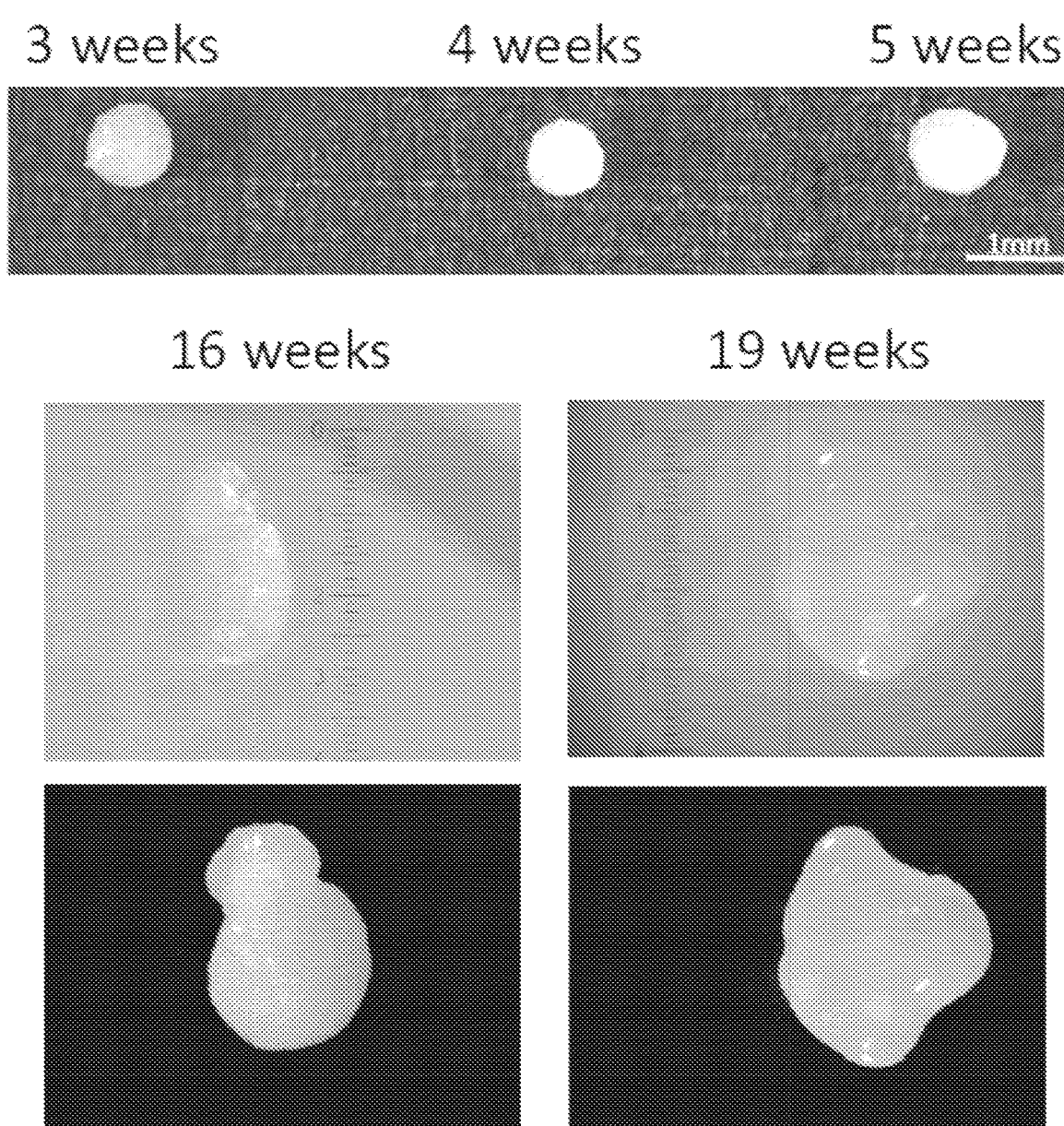

FIG. 8 shows photographs of hESC-derived cartilage pellets at 3 weeks, 4 weeks, 5 weeks, 16 weeks and 19 weeks.

Figure 9:
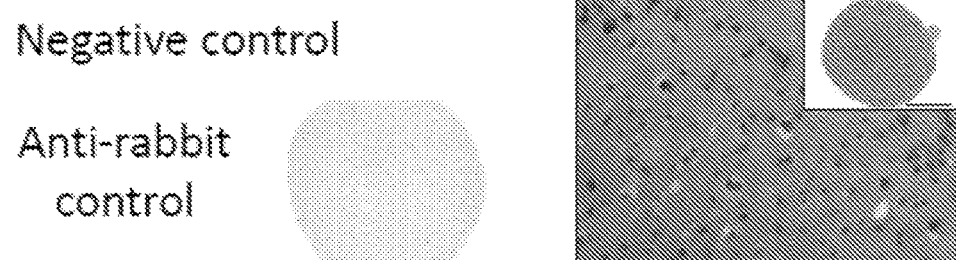

FIG. 9 shows immunohistochemistry of hESC-derived cartilage pellets at 3 weeks, 4 weeks and 5 weeks of culture demonstrating SOX9 and Type II collagen and the absence of Type I collagen and Safranin O staining.

Figure 10A:
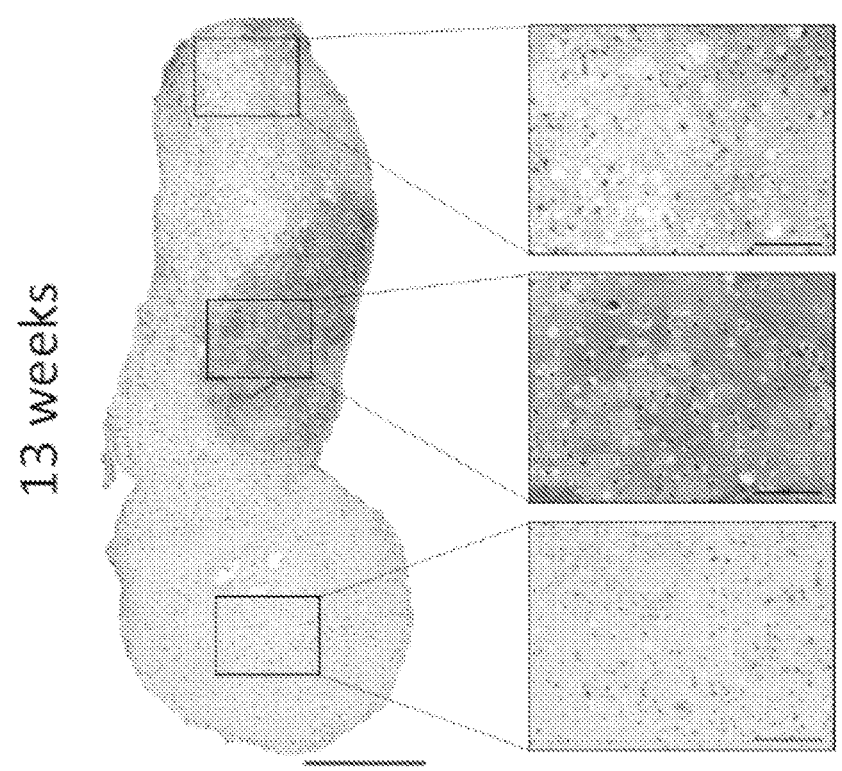
Figure 10B:
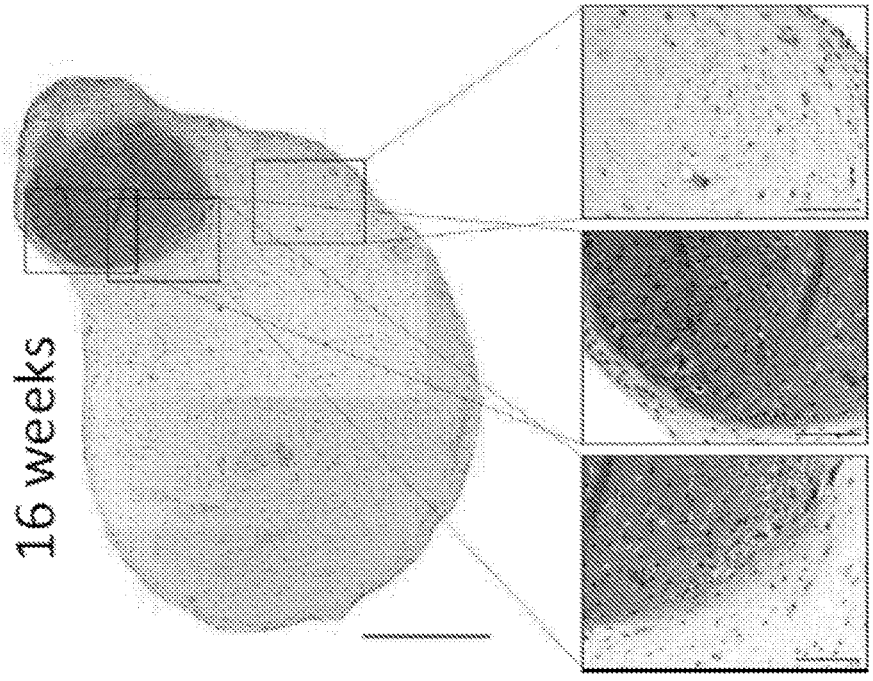
Figure 10C:
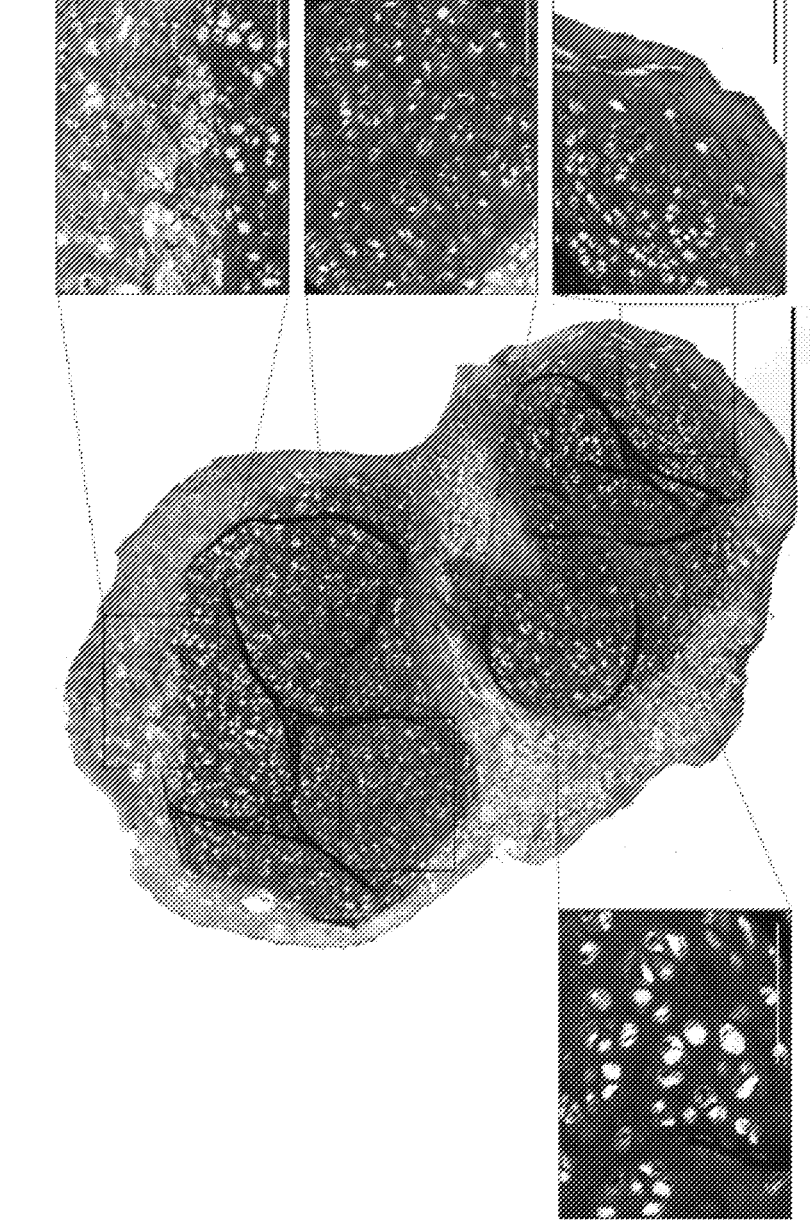

FIG. 10 shows Safranin O staining in hESC-derived cartilage pellet at 13 weeks (FIG. 10A), 16 weeks (FIG. 10B) and 19 weeks (FIG. 10C) of culture.

Figure 11A:
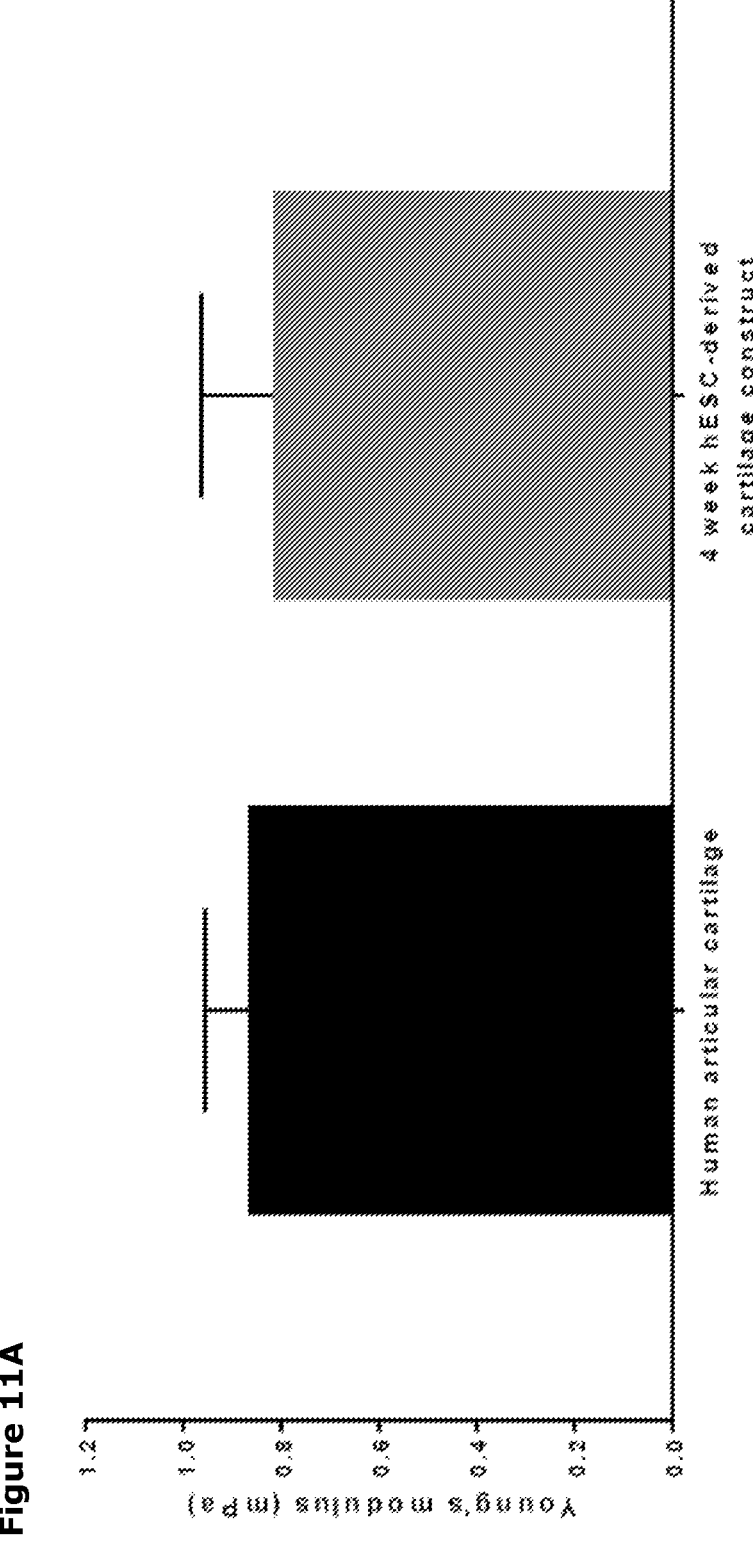
Figure 11B:
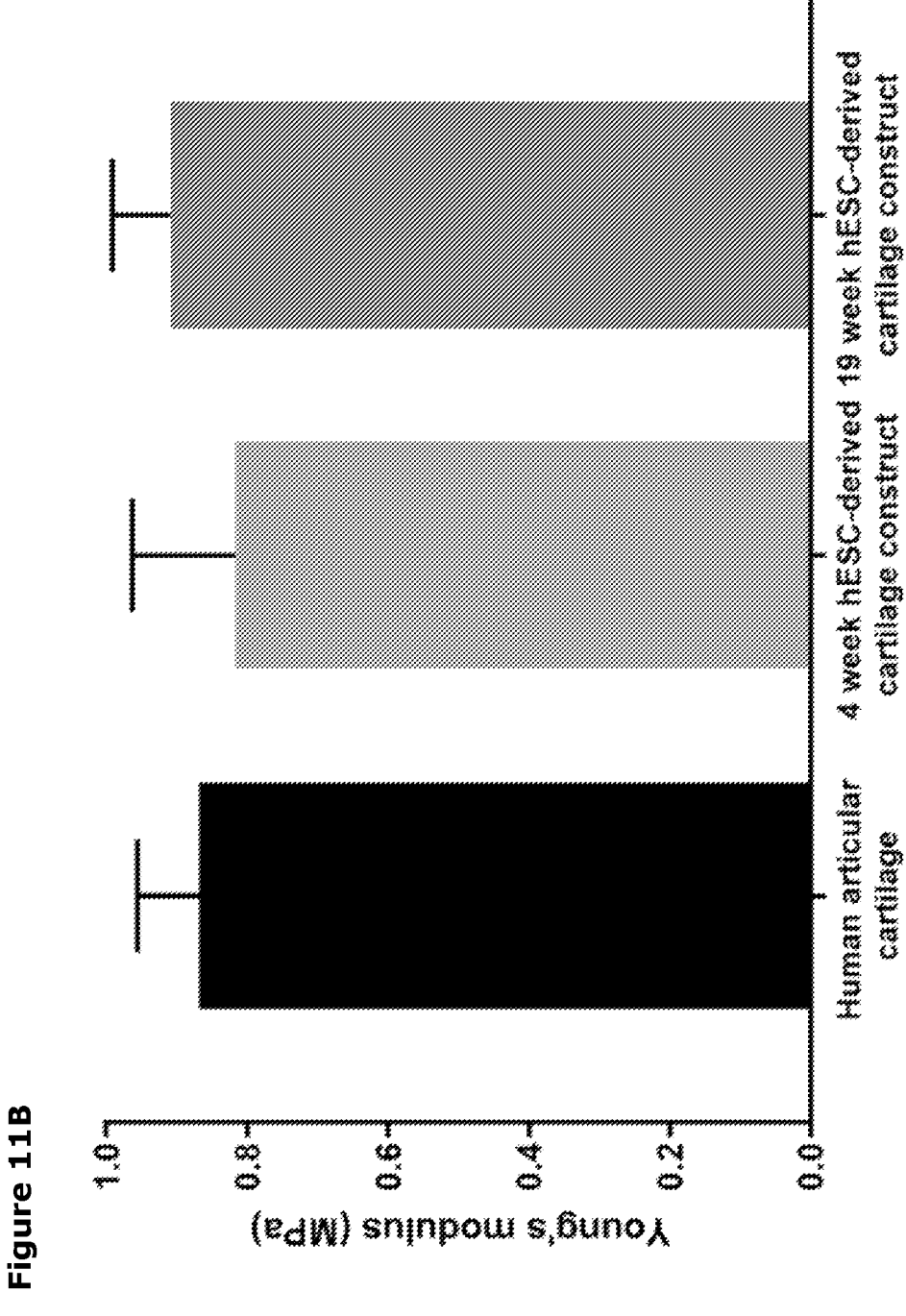

FIG. 11A shows the Young's moduli of human articular cartilage and 4-week hESC-derived cartilagepellets. Values represent mean±SEM. FIG. 11B shows the Young's moduli of human articular cartilage, 4-week and 19-week hESC-derived cartilage constructs (pellets). No significant differences were observed between human articular cartilage and the hESC-derived cartilage constructs. Values represent mean±SEM.

Figure 12A:
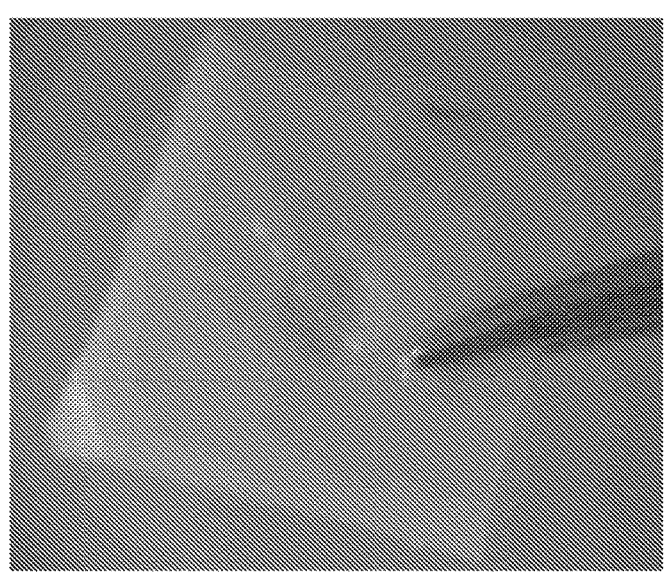
Figure 12B:
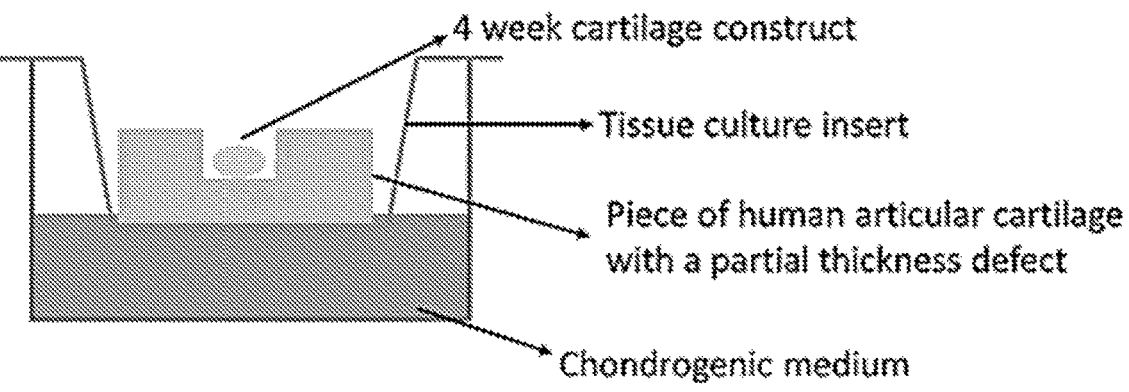

FIG. 12A shows a piece of full thickness, native human articular cartilage containing a partial thickness defect. FIG. 12B shows a schematic of the organotypic culture model.

Figure 13:
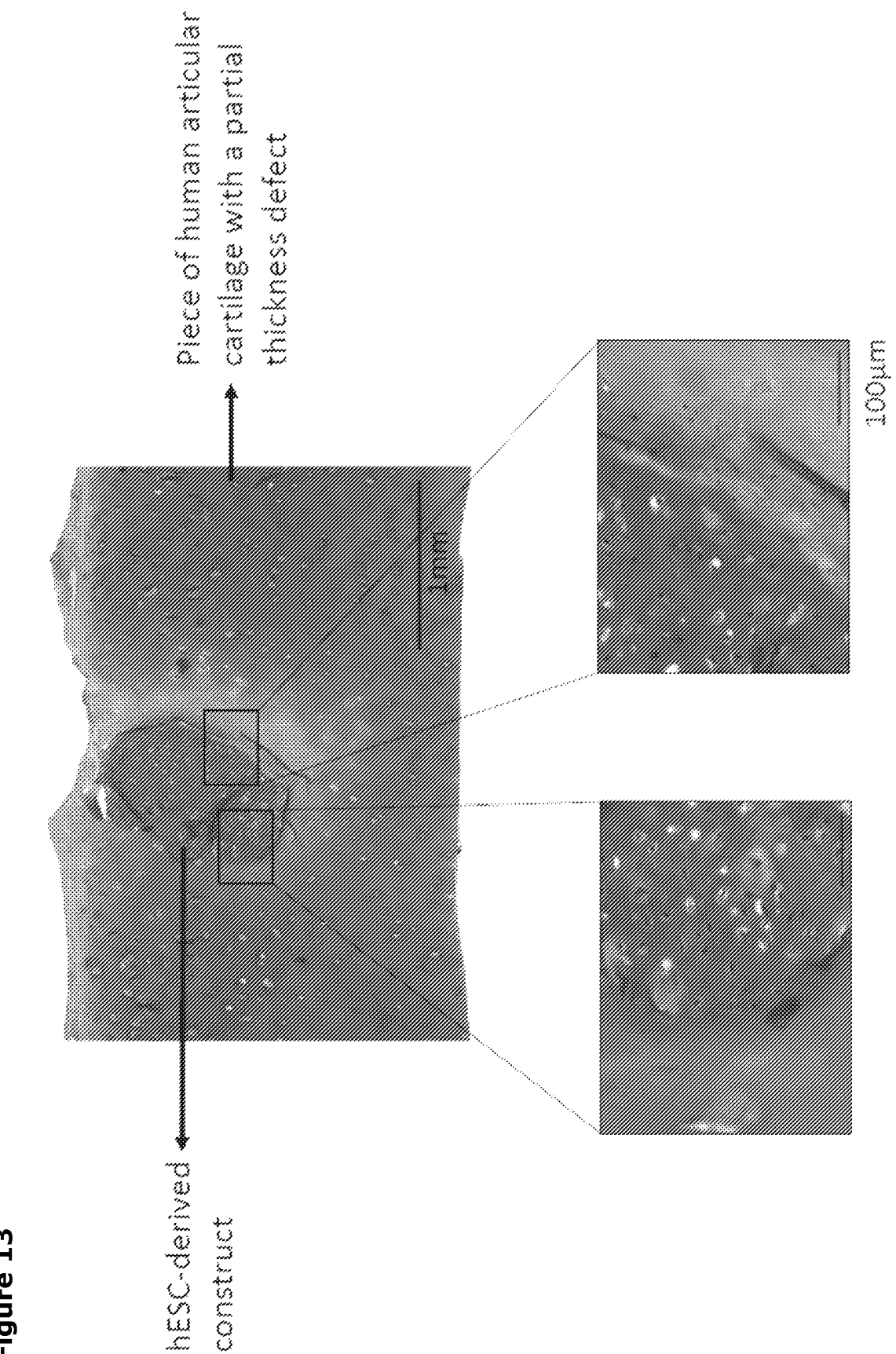

FIG. 13 shows integration of the hESC-derived cartilage with the native human articular cartilage within a partial thickness defect.

Figure 14:

FIG. 14 shows a photograph of hESC-derived cartilage cultured on a piece of native human articular cartilage.

Figure 15:
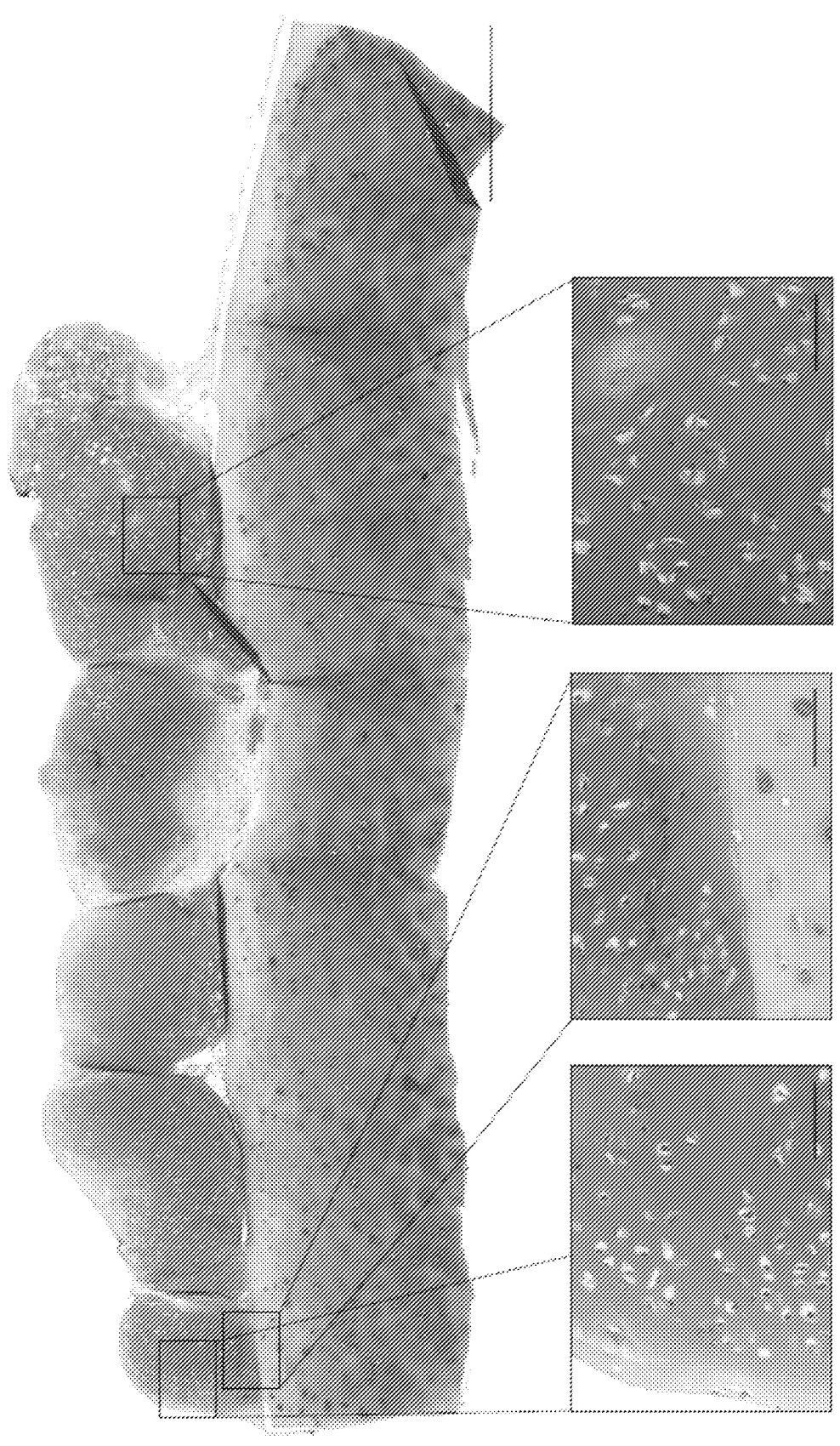

FIG. 15 shows Safranin O staining of the co-cultured hESC-derived cartilage and native human articular cartilage.

Figure 16:
Figure 16:
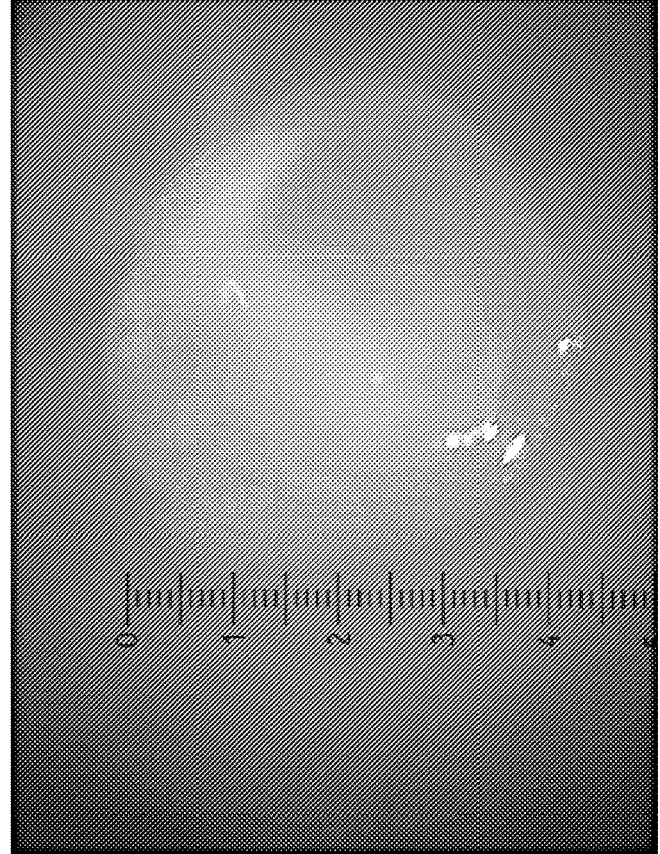

FIG. 16 shows photographs of hESC-derived cartilage (approximately 4.5 mm diameter) cultured on a Polyethylene Terephthalate (PET) membrane.

Figure 17A:
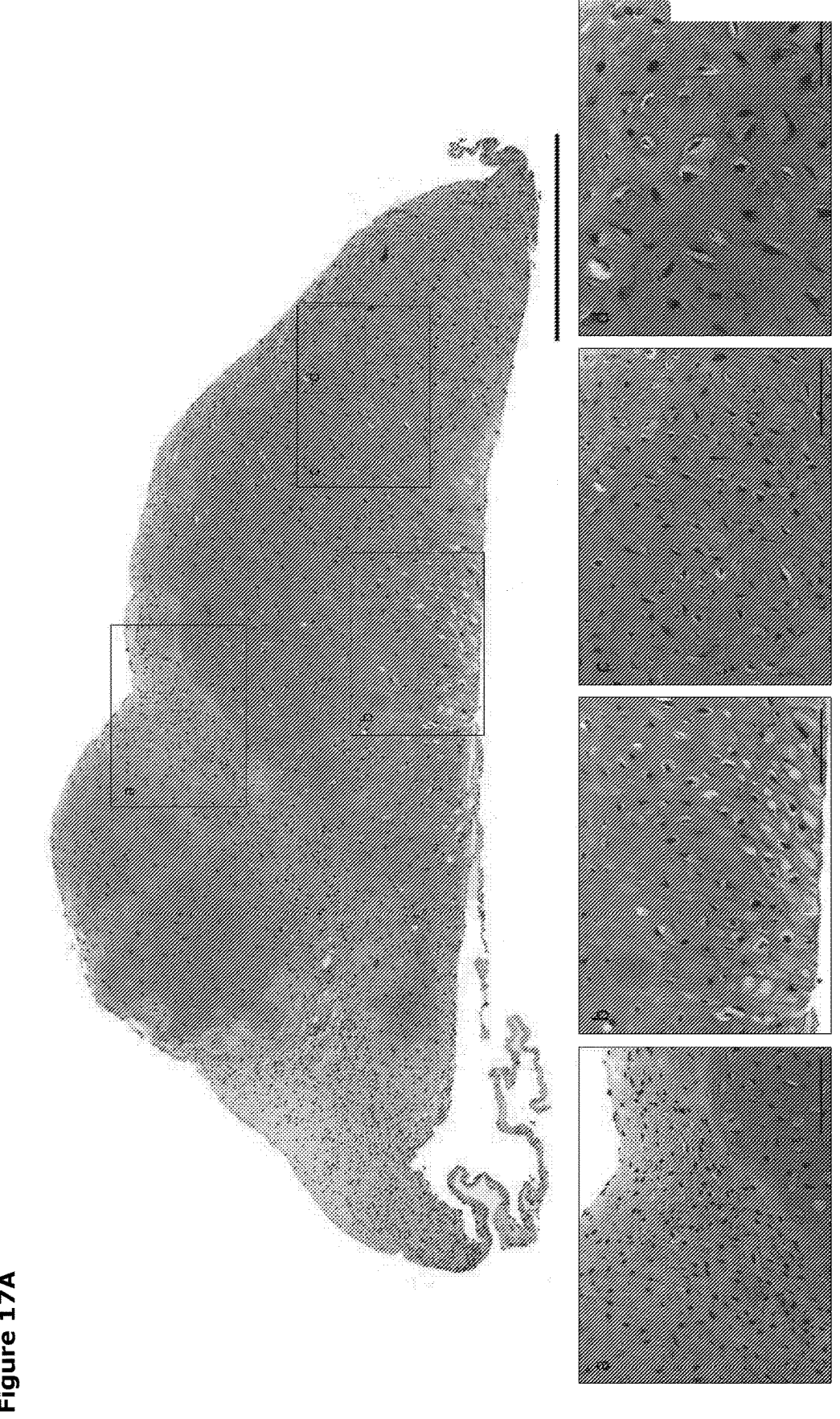
Figure 17B:
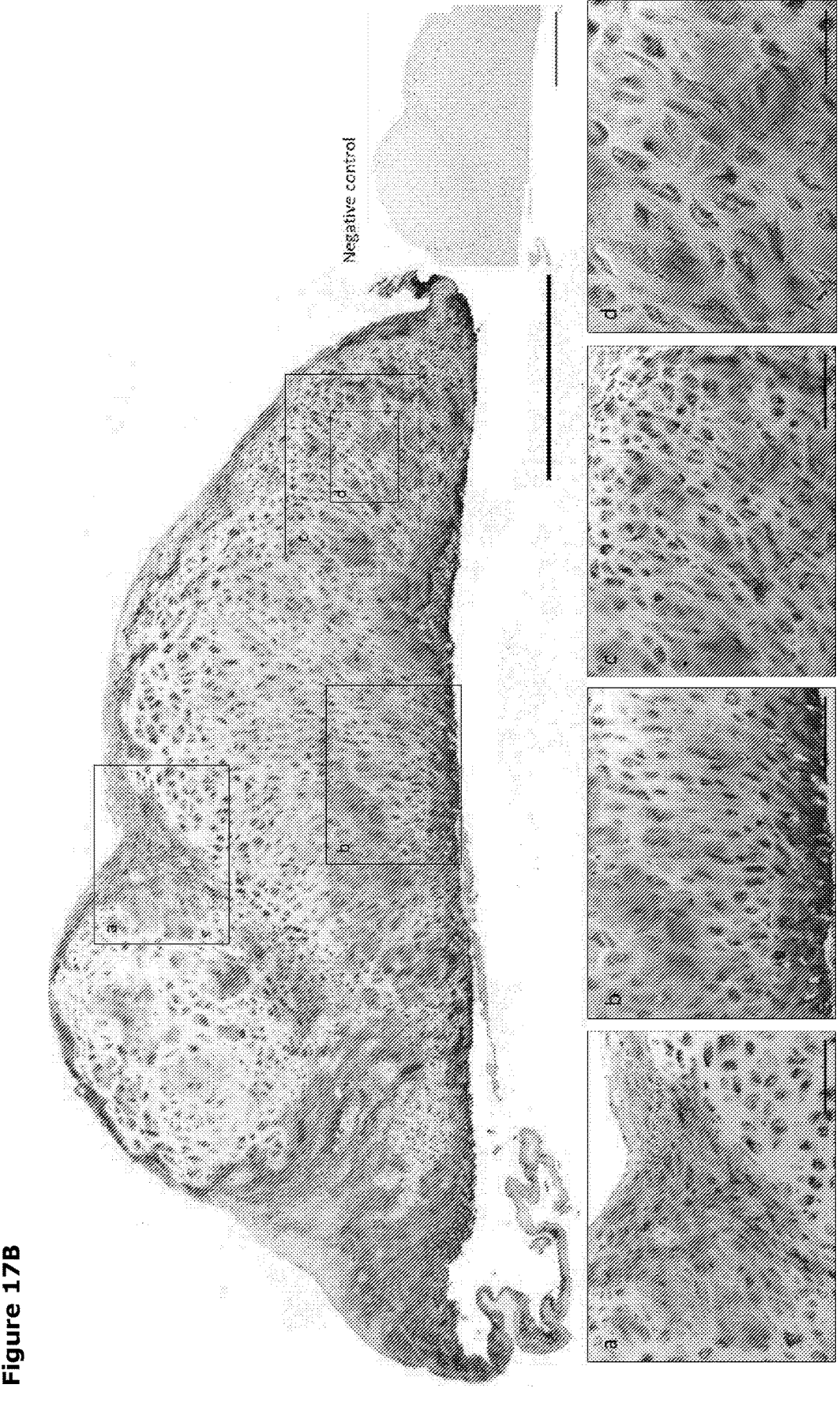

FIG. 17 shows Safranin O staining (FIG. 17A) and Aggrecan immunostaining (FIG. 17B) of hESC-derived cartilage cultured on a PET membrane. Scale bars represent 500 μm, 100 μm and 50 μm.

Figure 18:
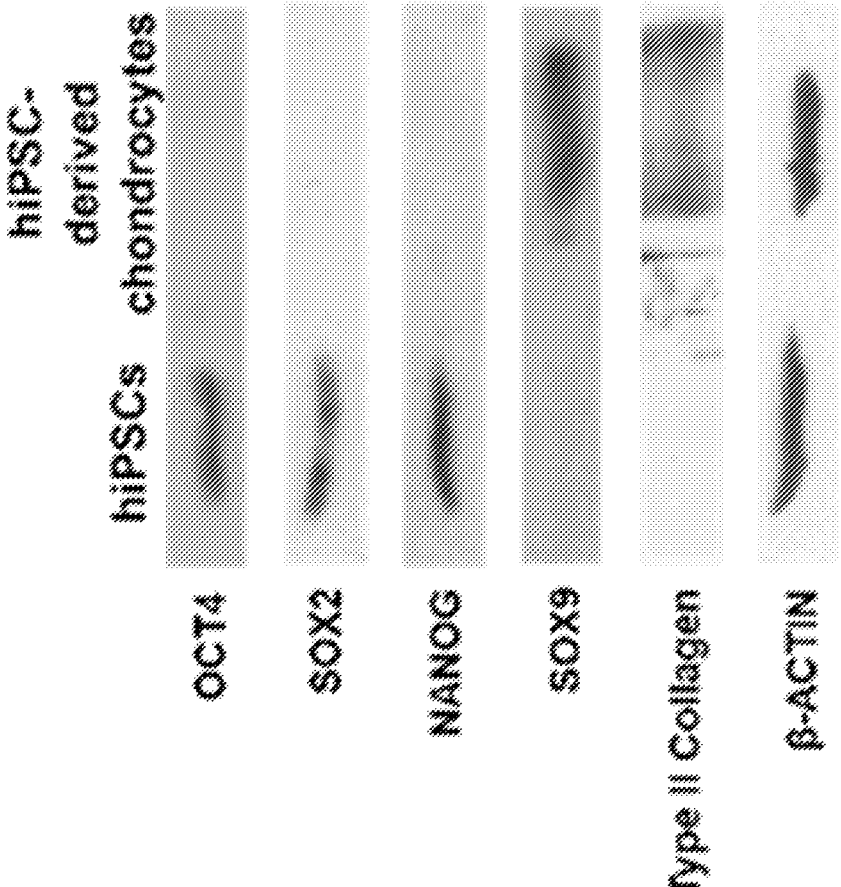

FIG. 18 shows Western Blots for proteins (OCT4, SOX2, NANOG, SOX9, Type II collagen and β-ACTIN (control)) present in hiPSCs (stage 0) and hiPSC-derived chondrocytes (stage 3).

Figure 19:
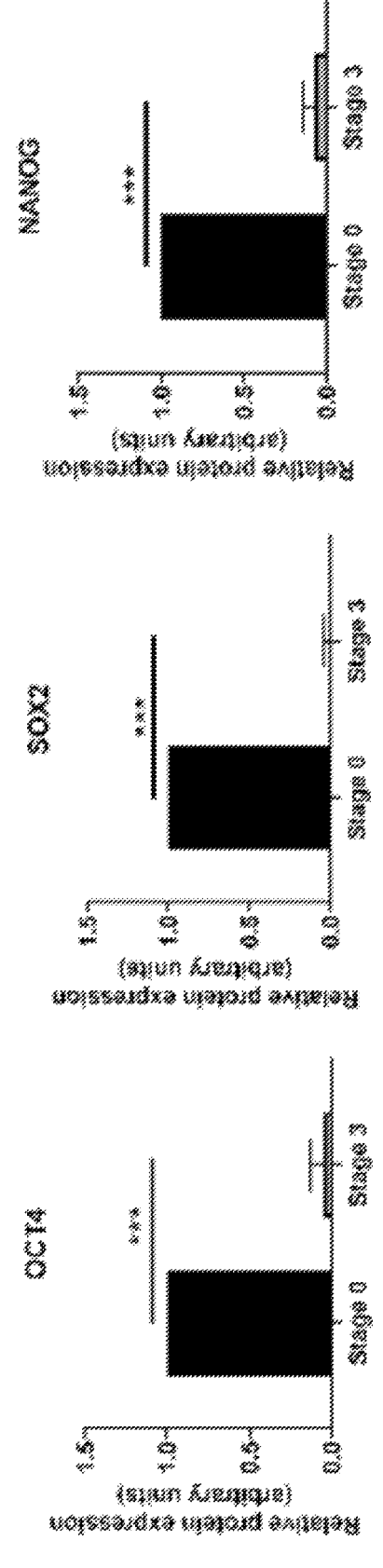
Figure 19:
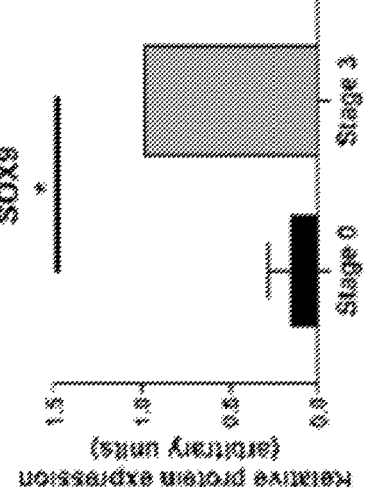

FIG. 19 shows bar charts which quantify the change in expression of OCT4, SOX2, NANOG, SOX9 and Type II collagen in hiPSCs (stage 0) and hiPSC-derived chondrocytes (stage 3). For OCT4, SOX2 and NANOG, data were normalised to β-ACTIN and stage 3 was compared to stage 0, which was set to 1. For SOX9 and Type II collagen, data were normalised to β-ACTIN and stage 0 was compared to stage 3, which was set to 1. Values represent mean±SD. Asterisks indicate a statistically significant difference. *$p \leq 10.05$, ***$p \leq 0.001$ (Student's t-test).

Figure 20:
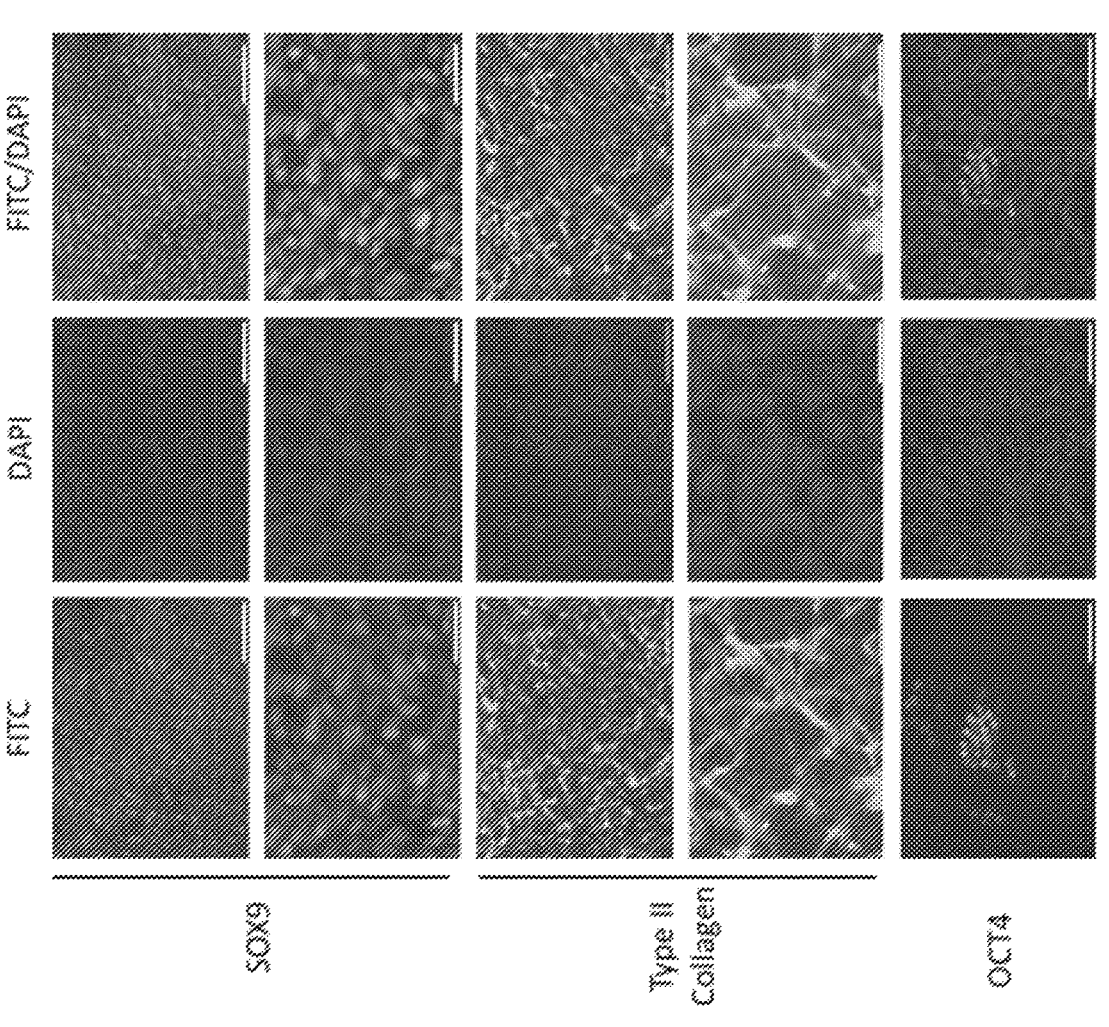

FIG. 20 shows immunocytochemistry of hiPSC-derived chondrocytes demonstrating robust SOX9 and Type II collagen expression, and the sporadic expression of OCT4. Scale bars for SOX9 and Type II collagen represent 200 μm and 50 μm; scale bar for OCT4 represents 100 μm.

Figure 21:
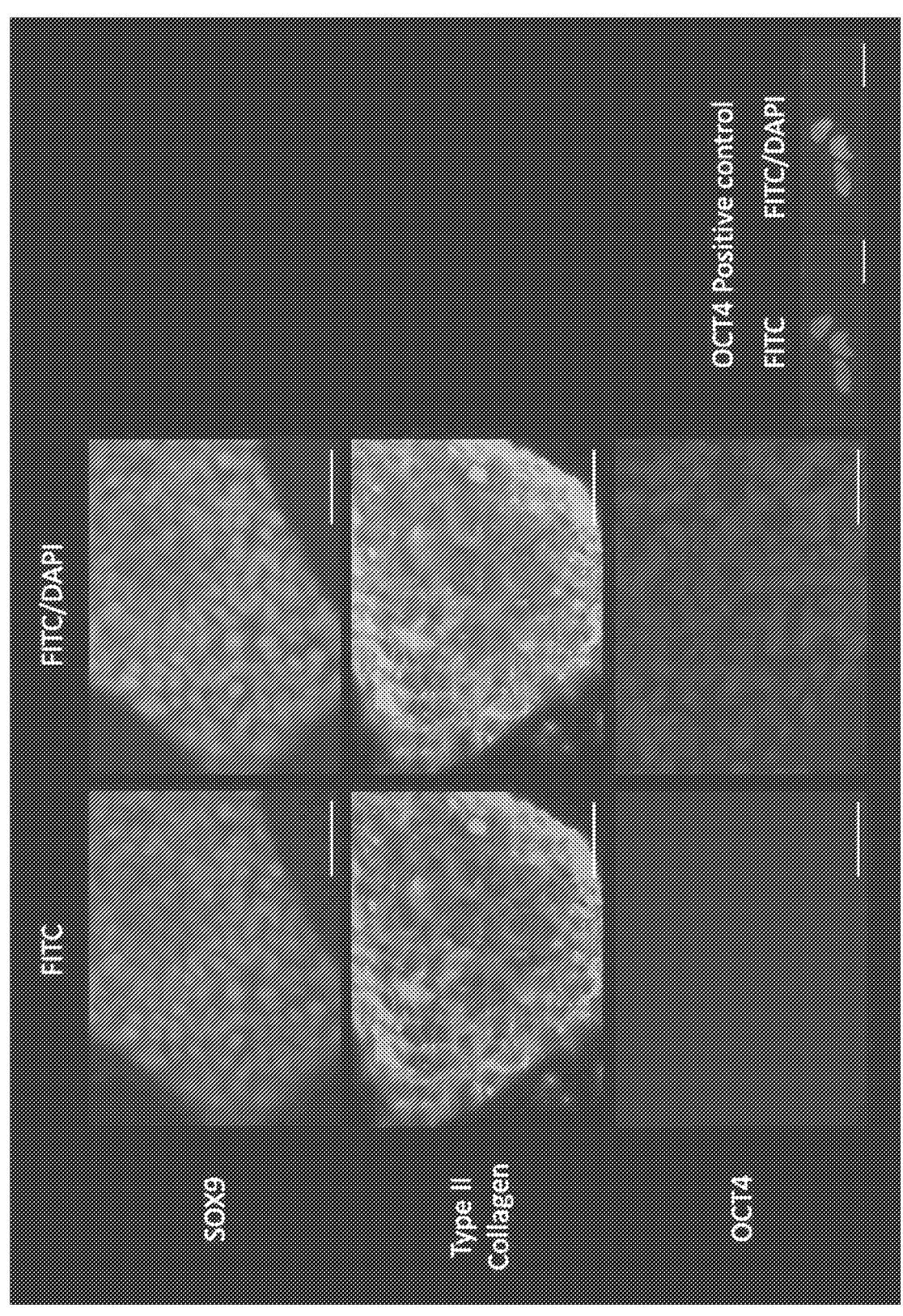

FIG. 21 shows immunocytochemistry of hiPSC-derived chondrocytes following culture on tissue culture plastic demonstrating robust SOX9 and Type II collagen expression, and the absence of OCT4 expression. Scale bars represent 50 μm.

EXAMPLES

Materials and Methods

ESC Culture and Differentiation

HUES7 hESCs were cultured under hypoxic conditions (5% $O_2$, 5% $CO_2$, and balanced nitrogen) as previously described in Christensen et al., 2015 (Scientific Reports 5 (17500): 1 to 14). A directed differentiation protocol based on that developed by Oldershaw et al. (2010. Nat Biotechnol. November; 28(11):1187-94. doi: 10.1038/nbt.1683) was used to generate hESC-derived chondrocytes. The method used directs cells through the developmental stages of primitive-streak/mesendoerm (day 4), to mesoderm (day 9), and ultimately to chondrocytes (day 14) using the temporal addition of specific growth factor cocktails containing varying concentrations of the following factors: Activin A, WNT3A, FGF2, BMP4, Follistatin, NT4, GDF5, and TGFβ₃. Here the differentiation protocol differs by the inclusion of TGF-$\beta_3$ (10 ng/ml) from day 9 onwards, culture on Matrigel (Corning) coated tissue culture plates, and continuous culture under hypoxic conditions (5% $O_2$ saturation). Cells were also passaged as colonies using collagenase dissociation rather than the trypsinization method described in Oldershaw et al. (2010. Nat Biotechnol. November; 28(11):1187-94. doi: 10.1038/nbt.1683) that used single cell culture. HUES7 hESCs were allowed to reach ~70% confluency before initiation of differentiation. Cartilage Generation Via Pellet Culture hESC-derived chondrocytes were dissociated and resuspended in chondrogenic media (α-MEM (Lonza) supplemented with 10 ng/ml TGF-$\beta_3$ (Peprotech), 10 nM dexamethasone (Sigma), 100 μM ascorbate-2-phosphate (Sigma), 0.35 mM L-Proline (Sigma) and 1×ITS supplement (Gibco)) containing $3 \times 10^5$ cells per 1 ml medium in a sterile universal tube. The cell suspension was centrifuged at 400 g for 5 minutes. Pellets were resuspended in 1 ml fresh chondrogenic media, and centrifuged as above. Pellets were cultured in a humidified incubator at 5% $O_2$, 5% $CO_2$, and balanced nitrogen for either 3, 4, 5, 13, 16 or 19 weeks.

Organotypic Cartilage Defect Culture

Near full-thickness articular cartilage pieces ($1 \times 1$ cm², 2 mm thick) were dissected from healthy non load-bearing regions of human femoral heads collected with approval of Southampton and South West Hampshire Research Ethics Committee (Ref. 210/01). A partial thickness defect (~$2 \times 2$ mm², 1 mm deep) was created in each articular cartilage piece with a sterile drill bit, taking extreme care to avoid full penetration of the cartilage. A single 4-week hESC-derived chondrocyte pellet (the neocartilage graft) was implanted into each defect and the neocartilage graft-host cartilage construct was then placed on a Millipore filter insert and cultured in chondrogenic medium at the air-liquid interface in a humidified atmosphere at 37° C., 5% $CO_2$ and 5% $O_2$ for 16 weeks. Pieces of articular cartilage with empty defects cultured for 16 weeks served as controls. The samples were harvested, fixed in 4% paraformaldehyde (PFA) overnight at 4° C. and processed for histological analysis according to Li et al., 2014 (Lab on a Chip 14: 4475-4485).

Organotypic Co-Culture Model

Near full-thickness articular cartilage pieces ($1 \times 1$ cm², 2 mm thick) were dissected from healthy non load-bearing regions of human femoral heads. A single 4-week hESC-derived chondrocyte pellet was placed on top of the piece of articular cartilage and co-cultured in chondrogenic medium on a Millipore filter insert at the air-liquid interface in a humidified atmosphere at 37° C., 5% $CO_2$ and 5% $CO_2$ for 16 weeks. The sample was harvested, fixed in 4% PFA overnight at 4° C. and processed for histological analysis according to Li et al., 2014.

Safranin O staining was performed as described previously (Tare et al., 2005 Biochemical and Biophysical Research Communications 333: 609-621).

Immunocytochemistry

Samples were analysed for immunocytochemistry as previously described (Christensen et al., 2015). Primary antibodies against OCT4 (Santa Cruz) 1:100, SOX2 (Cell Signalling Technology) 1:200, NANOG (Abcam) 1:100, TRA-1-60 (Santa Cruz) 1:100, SOX9 (Millipore) 1:150, Type II Collagen (Calbiochem) 1:500 were used.

Immunohistochemistry

Samples were analysed for immunohistochemistry as previously described (Li et al., 2014). Primary antibodies against SOX9 (1:150), Collagen Type I (1:1000) and Collagen Type II (1:500) were used.

Western Blotting

Samples for Western blotting were analysed as previously described (Christensen et al., 2015). Primary antibodies against OCT4 (1:1000), SOX2 (1:3000), NANOG (1:500) and SOX9 (1:850), Type II Collagen (1:1000), β-actin (Sigma) 1:50,000 were used.

Mechanical Testing

A custom-built mechanical testing rig was used to compress samples between two flat metal plates. The device generated force and displacement readings used to determine the Young's elastic modulus (E) for each sample. For native cartilage, 5 mm² samples of full thickness articular cartilage were harvested from the non-load bearing region of the femoral head. hESC-derived chondrocyte pellets were tested following 4 or 19 weeks culture.

Example 1—Characterisation of Human Embryonic Stem Cells (hESCs) by Immunocytochemistry The hESCs, which would be used to create chondrocytes, were analysed. It was confirmed that they express the biomarkers OCT4, SOX2, NANOG and TRA-1-60. Thus they are deemed to be hESCs.

Example 2—Protocol for the Production of hESC-Derived Chondrocytes

Figure 2:
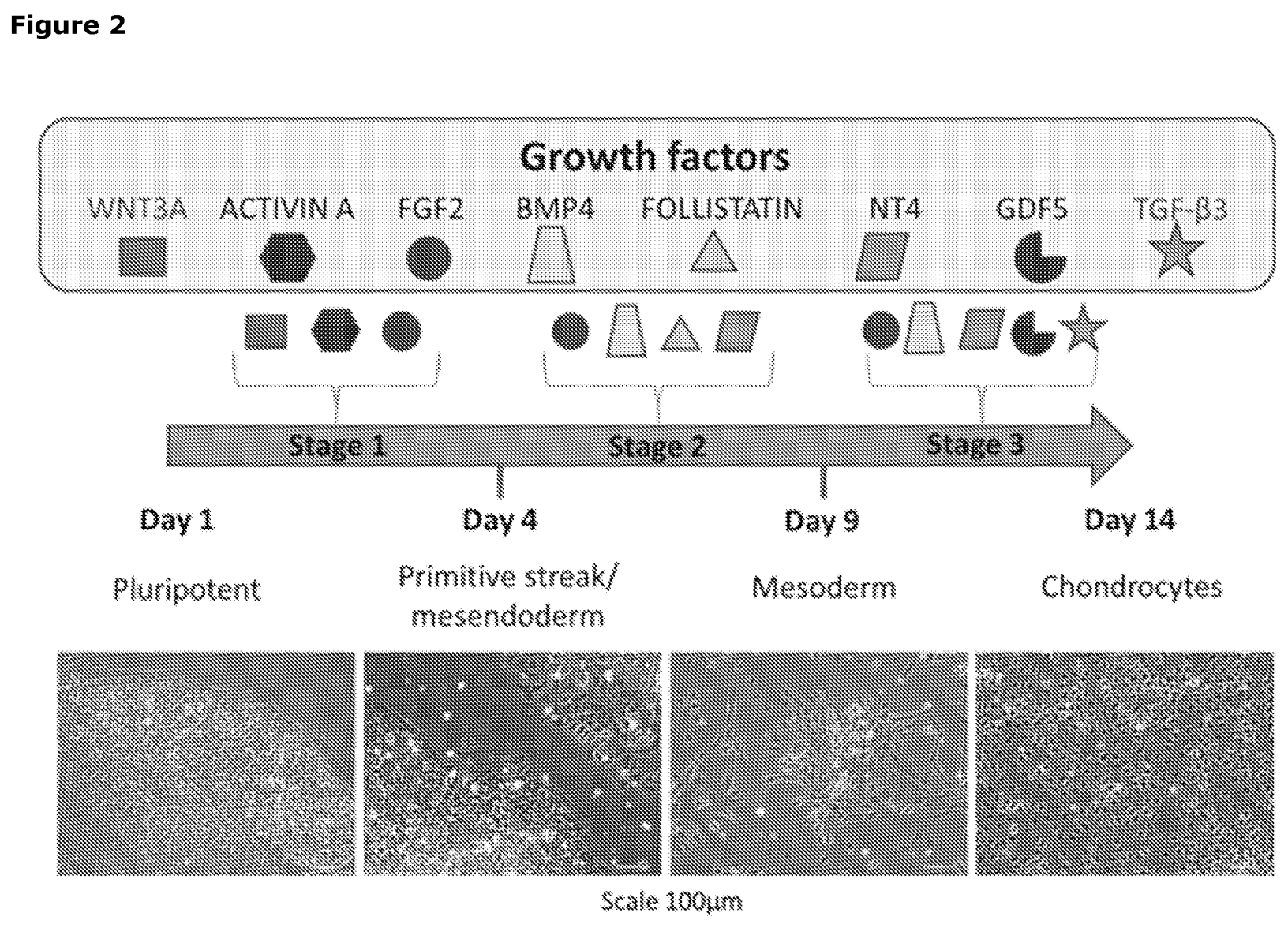

In order to differentiate the pluripotent, hESCs into chondrocytes they were temporarily cultured in media comprising three different mixtures of growth factors (see FIG. 2).

The first mixture was used to create a mesendodermic culture media. It comprises WNT3A, Activin A and FGF2, and was used to differentiate the hESCs (stage 0) into primitive streak/mesendoderm (stage 1).

After 4 days of culture (day 0 to day 4), the first mixture of growth factors was replaced by a second mixture, which was used to create a mesodermic culture media. The second mixture comprises FGF2, BMP4, Follistatin and NT4, and was used to differentiate the primitive streak/mesendoderm (stage 1) into a mesoderm (stage 2).

After 5 days of culture (day 4 to day 9), the second mixture was replaced with a third mixture, which was used to create a chondroinductive culture media. The third mixture comprises FGF2, BMP4, NT4, GDF5 and TGF-β3, and was used to differentiate the mesoderm (stage 2) into chondrocytes (stage 3).

Example 3—Characterisation of hESC-Derived Chondrocytes

Figure 3:
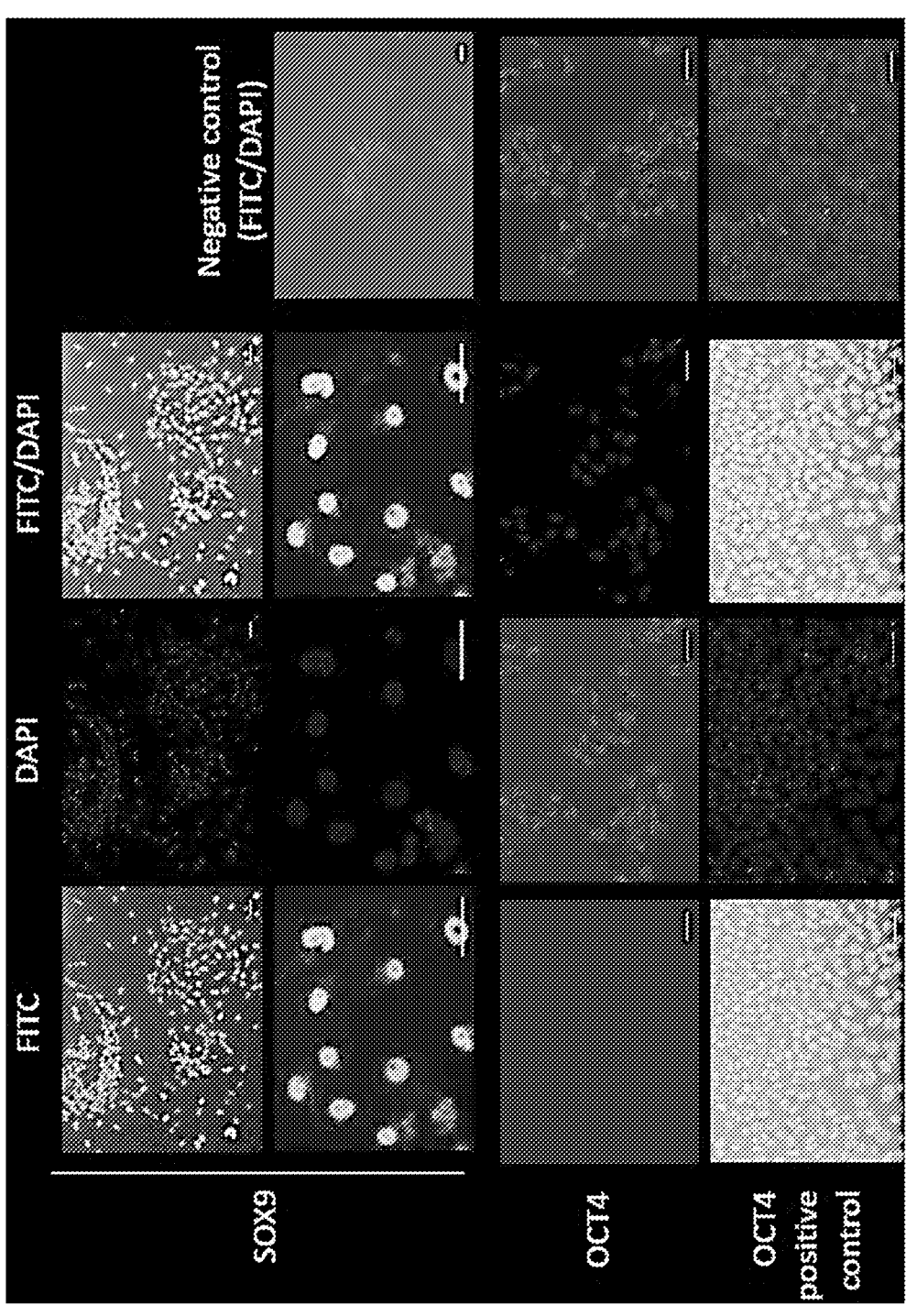
FIG. 3 shows immunocytochemistry of hESC-derived chondrocytes demonstrating SOX9 expression and the absence of OCT4.
Figure 4:
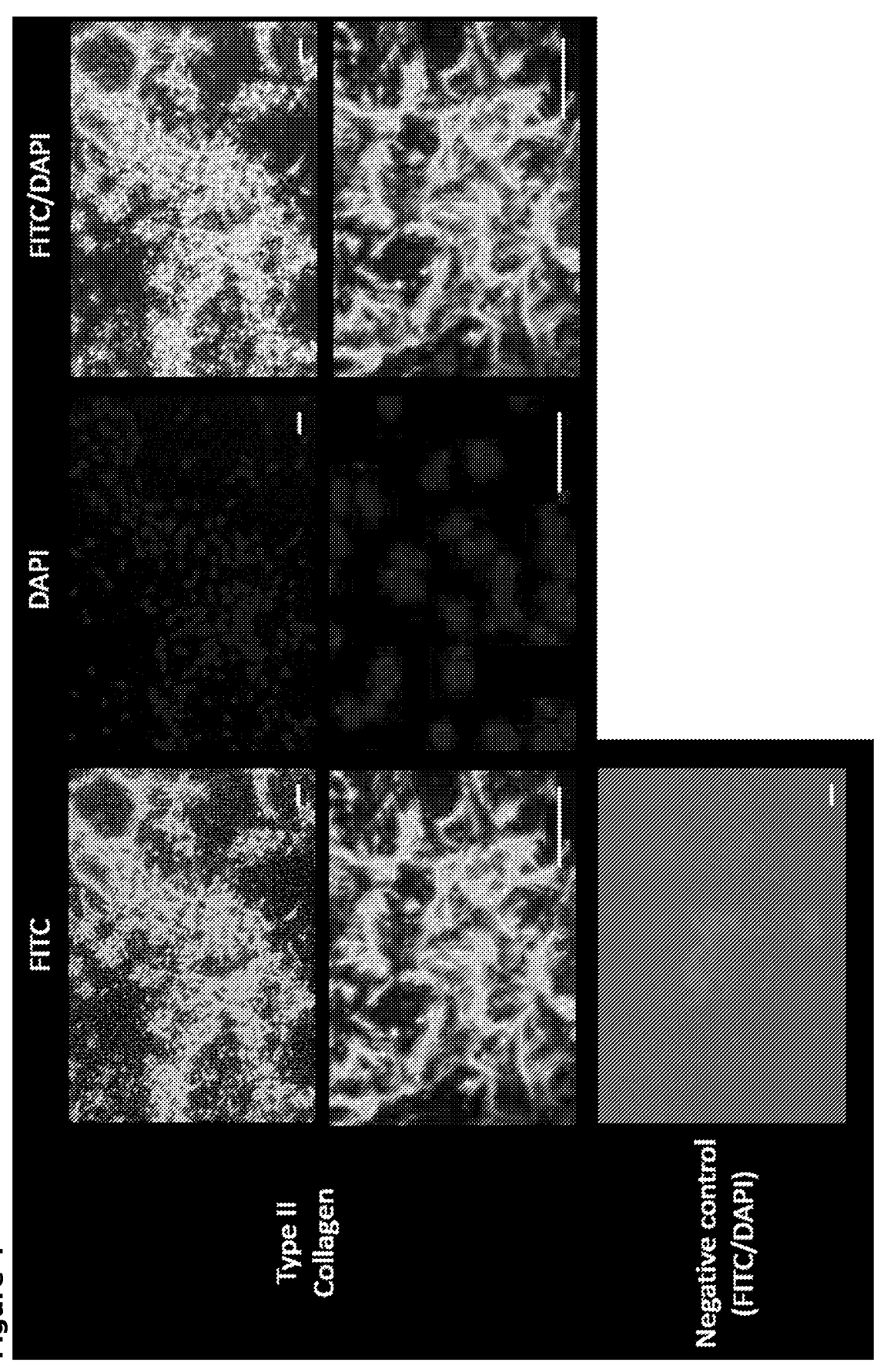
FIG. 4 shows immunocytochemistry of hESC-derived chondrocytes demonstrating Type II collagen expression in the extracellular matrix.

In order to confirm that the hESCs have differentiated into chondrocytes, the stage 3 cells were analysed (by immunohistochemistry) to determine if they express the chondrogenic transcription factor, SOX9. It was found that the hESC-derived chondrocytes do express SOX9 but do not express, OCT4, which is a key pluripotency transcription factor and marker of hESCs (see FIG. 3). Moreover, the chondrocytes synthesise an extracellular matrix that is rich in Type II collagen, a cartilage specific collagen (see FIG. 4).

Figure 5:
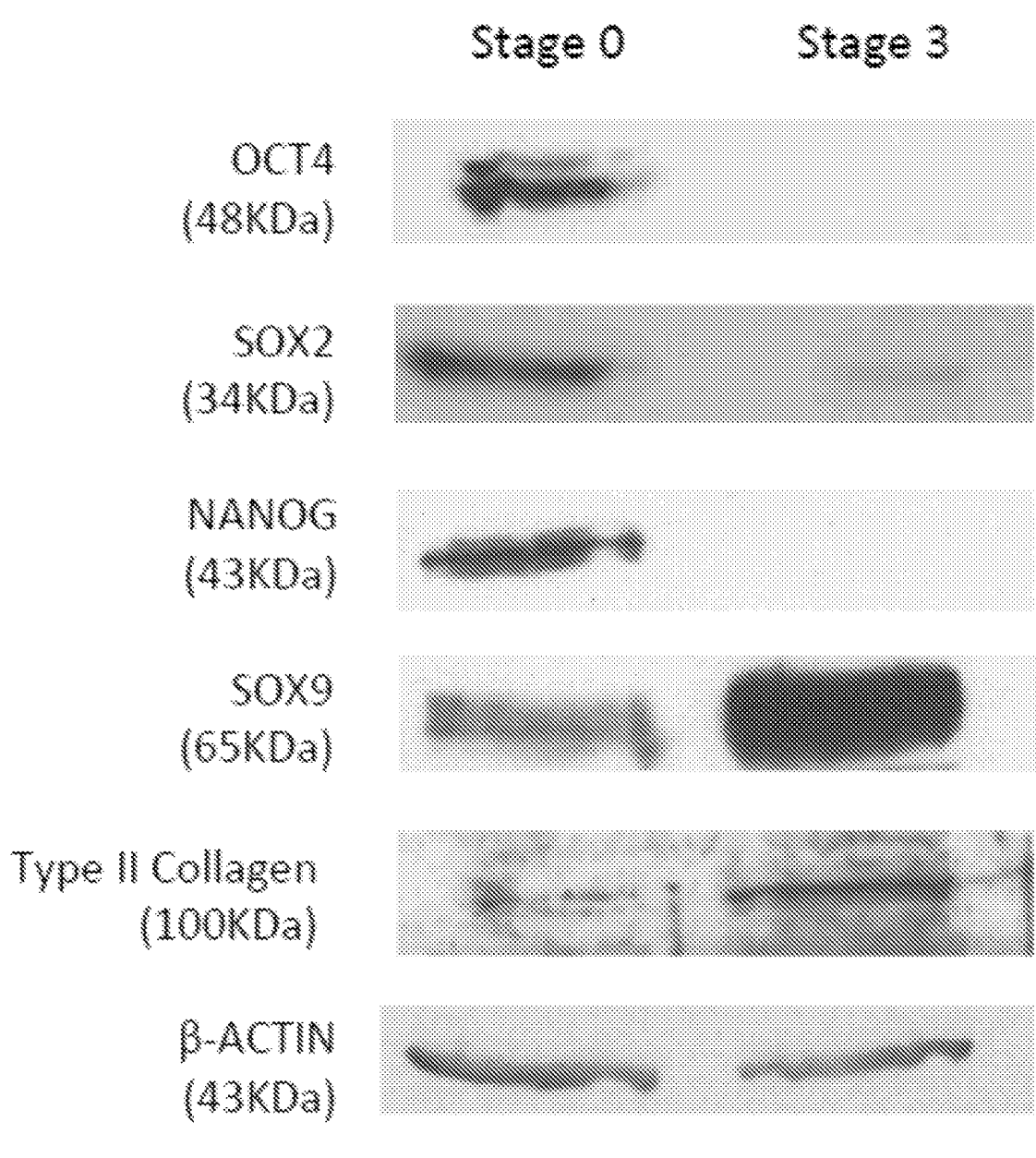
FIG. 5 shows a Western Blot for proteins (OCT4, SOX2, NANOG, SOX9, Type II collagen and β-actin (control)) present in hESCs (stage 0) and hESC-derived chondrocytes (stage 3).
Figure 6A:
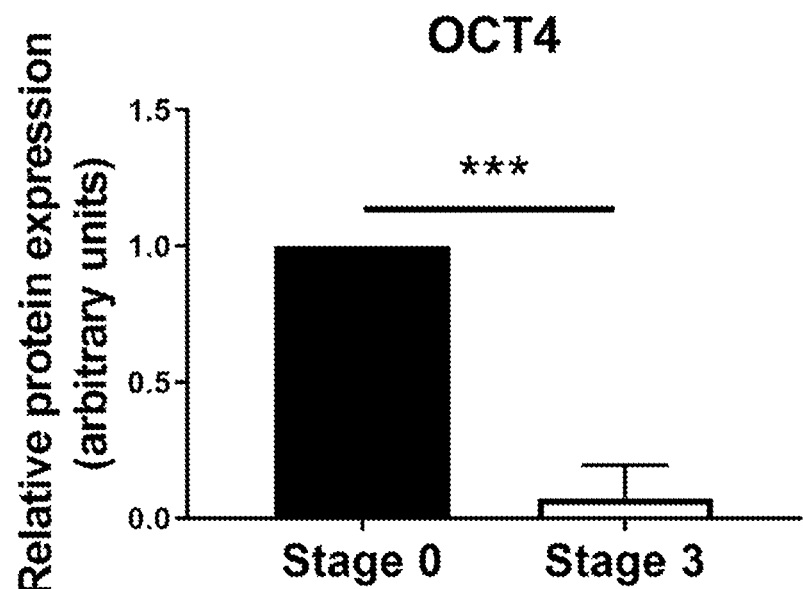
Figure 6B:
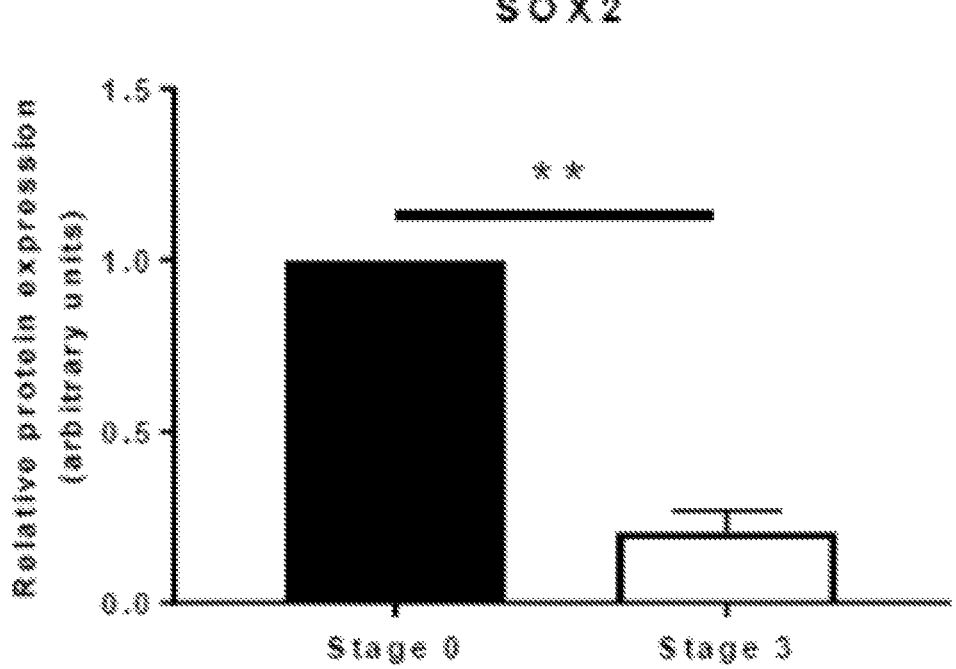
Figure 6C:
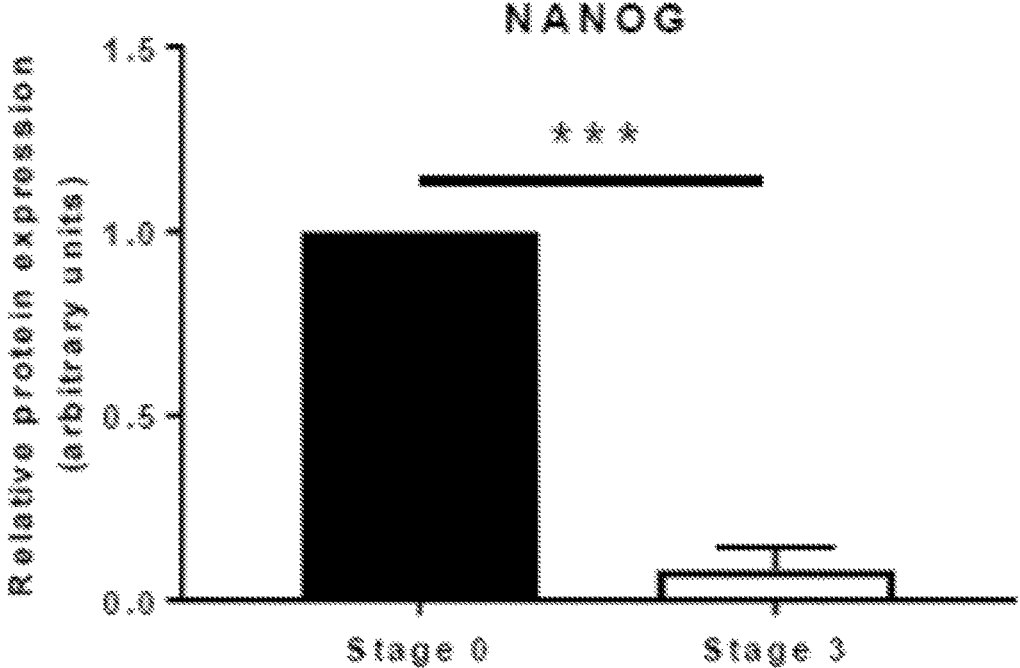
Figure 6D:
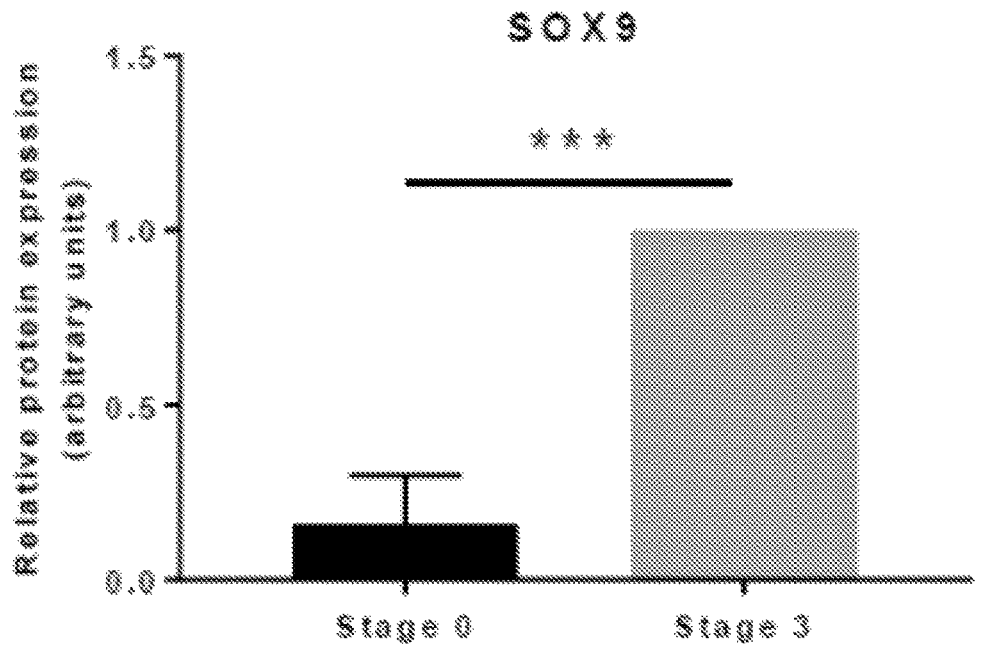
Figure 6E:
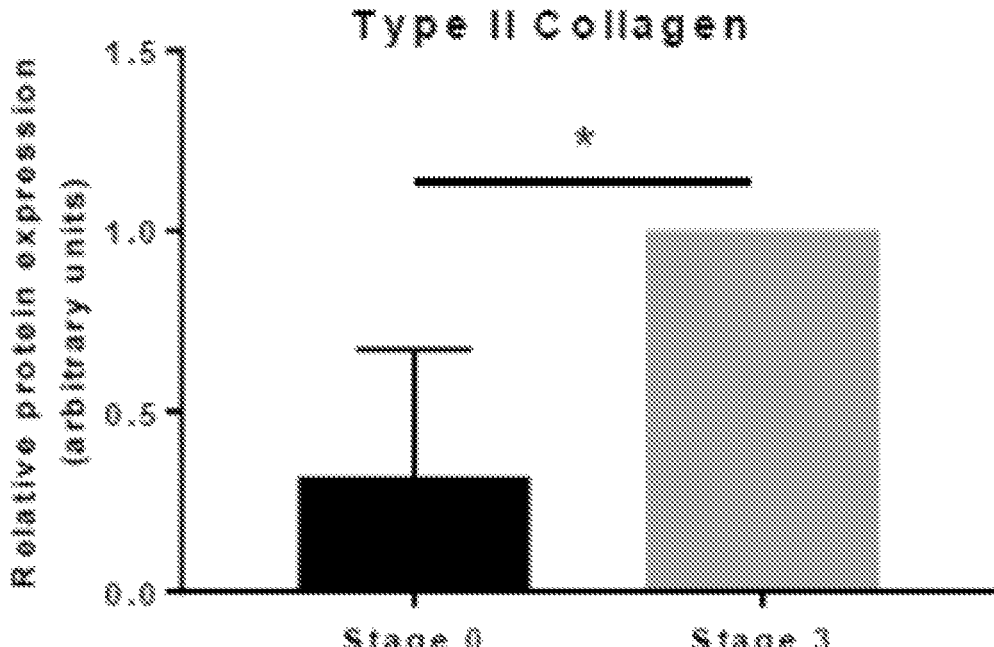

These results above were confirmed by Western Blot (see FIG. 5) and quantified in FIG. 6. The Western Blots also confirmed that the stage 3 cells have negligible expression of OCT4, SOX2 and NANOG proteins, while SOX9 and Type II collagen are significantly increased. β-ACTIN expression was used as a control. It is present in hESCs (stage 0) and hESC-derived chondrocytes (stage 3).

These results confirm that the stage 3 cells are no longer hESCs, and that they are in fact chondrocytes.

Example 4—Schematic Representation of the Method of Pellet Culture

A schematic representation of the protocol used to culture a mass of hESC-derived chondrocytes is provided in FIG. 7.

Step 1—provide a suspension of the stage 3 hESC-derived chondrocytes in a vessel with a pointed base.

Steps 2 and 3—centrifuge the chondrocytes so that they form a pellet in the pointed base of the relevant vessel.

Step 4—remove the media in which the cells were suspended in order leave behind the pellet of cells.

Step 5—culture the pellet of cells in chondrogenic medium, under hypoxic conditions for approximately 21 days.

Example 5—Photographs of hESC-Derived Cartilage Pellets

It has been found that 3D cartilage tissue is produced by a pellet of hESC-derived chondrocytes after at least three weeks in culture under hypoxic conditions. hESC-derived cartilage pellets cultured for 3 weeks, 4 weeks, 5 weeks have a diameter of approximately 1 mm, while pellets cultured for 16 weeks and 19 weeks have a diameter of approximately 3 mm (see FIG. 8).

Example 6—Characterisation of hESC-Derived Cartilage Pellets hESC-derived cartilage pellets were analysed after 3 weeks, 4 weeks and 5 weeks of culture. The pellets express SOX9 and Type II collagen, which indicates the presence of cartilage (FIG. 9). However, the pellets do not express Type I collagen or Safranin O staining. FIG. 10 shows Safranin O staining of hESC-derived cartilage pellet at 13 weeks (FIG. 10A), 16 weeks (FIG. 10B) and 19 weeks (FIG. 10C) of culture. At 19 weeks the hESC-derived cartilage pellet displays robust Safranin O staining and typical hyaline cartilage morphology (chondrocytes in lacunae embedded in dense extracellular matrix).

Example 7—Measurement of Biomechanical Properties of Full Thickness Articular Human Cartilage, 4-Week and 19-Week hESC-Derived Cartilage Pellets (Constructs)

The Young's moduli were determined in human articular cartilage, 4-week and 19-week hESC-derived cartilage pellets (constructs). The average value for the Young's modulus of full thickness articular human cartilage is comparable to that of 4-week and 19-week hESC-derived cartilage pellets (see FIG. 11A and FIG. 11B).

Example 9—Organotypic Culture System to Model Repair of Partial Thickness Defect in Human Articular Cartilage FIG. 12A shows a piece of full thickness, native human articular cartilage containing a partial thickness defect. The hESC-derived cartilage construct was placed in the partial thickness defect created in a piece of full thickness native human articular cartilage. This was then placed on a tissue culture insert and cultured at the air liquid interface (for 16 weeks), in chondrogenic medium (FIG. 12B). The hESC-derived cartilage integrated into the host native cartilage and contributed to the repair of the partial thickness defect (see FIG. 13).

Example 10—Scale Up of hESC-Derived Cartilage Generation

FIG. 14 shows an approximately 1 cm$^2$ piece of hESC-derived cartilage generated by culturing a 1 mm 4-week hESC-derived cartilage pellet on full thickness native human articular cartilage in chondrogenic medium for 16 weeks.

Example 11—Safranin O Staining of the Co-Cultured hESC-Derived Cartilage and Native Human Articular Cartilage Robust Safranin O staining is present in both the scaled-up hESC-derived cartilage and the native human articular cartilage. The hESC-derived cartilage exhibits typical hyaline cartilage morphology comprising of chondrocytes in lacunae embedded in dense extracellular matrix (see FIG. 15).

Example 12—Photographs of hESC-Derived Cartilage Cultured on a Polyethylene Terephthalate (PET) Membrane FIG. 16 shows an approximately 4.5 mm diameter hESC-derived cartilage construct generated by culturing a 4-week hESC-derived cartilage pellet on a PET membrane in chondrogenic medium for 16 weeks. Robust Safranin O staining (FIG. 17A) and Aggrecan expression (FIG. 17B) is present in the hESC-derived cartilage construct. The hESC-derived cartilage construct exhibits typical hyaline cartilage morphology comprising of chondrocytes in lacunae embedded in dense extracellular matrix (see FIGS. 17A and B).

Example 13—Characterisation of hiPSC-Derived Chondrocytes

Chondrocytes have been generated from human induced pluripotent stem cells (hiPSCs). The NIBSC-8 hiPSC cell line was used, but other hiPSC lines may be used. hiPSCs were cultured on a substrate, vitronectin, in Essential 8 medium under hypoxic conditions (5% $O_2$, 5% $CO_2$, and balanced nitrogen). hiPSCs were differentiated into hiPSC-derived chondrocytes on vitronectin-coated plates using a directed differentiation protocol based on that used to generate hESC-derived chondrocytes. The method used directs cells through the developmental stages of primitive-streak/mesendoerm (day 4), to mesoderm (day 9), and ultimately to chondrocytes (day 14) using the temporal addition of specific growth factor cocktails containing varying concentrations of the following factors: Activin A, WNT3A, FGF2, BMP4, Follistatin, NT4, GDF5, and TGFβ3.

In order to confirm that the hiPSCs have differentiated into chondrocytes, the stage 3 cells were analysed for OCT4, SOX2, NANOG, SOX9 and Type II collagen by Western blotting (FIG. 18). Quantification of the Western blots confirmed that the stage 3 cells have negligible expression of OCT4, SOX2 and NANOG proteins, while expression of SOX9 and Type II collagen increased significantly (FIG.

19). β-ACTIN expression was used as a control. It is present in hiPSCs (stage 0) and hiPSC-derived chondrocytes (stage 3).

Immunocytochemistry was used to investigate the expression of SOX9, Type II collagen and OCT4 in hiPSC-derived chondrocytes. Robust expression of SOX9 and Type II collagen was observed in the hiPSC-derived chondrocytes. However, sporadic expression of OCT4 was also observed (FIG. 20).

To eliminate OCT4 expression, hiPSC-derived chondrocytes on day 14 were passaged onto tissue culture plastic and cultured under hypoxic conditions in chondroinductive medium for a further 3 days. Immunocytochemistry of hiPSC-derived chondrocytes (day 17) demonstrated absence of OCT4 protein expression, while expression of SOX9 and Type II collagen persisted (FIG. 21). This demonstrates the generation of a robust, homogeneous population of hiPSC-derived chondrocytes.

PSC Growth Medium Examples mTESR™ Comprises:

DMEM/F12; L-ascorbic acid; Selenium; Transferrin; NaHCO$_3$; Insulin; FGF2; TGFB1; Albumin (BSA); Glutathione; L-glutamine; Defined lipids; Thiamine; Trace Elements B; Trace Elements C; Beta-mercaptoethanol; Pipecolic acid; LiCl; GABA; and H$_2$O.

Essential 8™ Comprises:

DMEM/F12; L-ascorbic acid; Selenium; Transferrin; NaHCO$_3$; Insulin; FGF2; and TGFB1.

All references described herein are incorporated by reference.

The invention claimed is:

1. A method for producing cartilage from pluripotent stem cells (PSCs) under hypoxic conditions, the method comprising:

providing PSCs;

culturing the PSCs under hypoxic conditions in a first culture medium comprising a Wingless/Integrated (WNT) family member, an Activin family member, and a Fibroblast Growth Factor (FGF) family member, thereby-inducing differentiation of the PSCs-into a primitive streak/mesendoderm;

culturing the primitive streak/mesendoderm under hypoxic conditions in a second culture medium comprising a FGF family member, a bone morphogenetic protein (BMP) family member, Follistatin, and a Neurotrophin (NT), thereby inducing differentiation of the primitive streak/mesendoderm into by a mesoderm;

culturing the mesoderm under hypoxic conditions in a third culture medium comprising an FGF family member, a BMP family member, an NT, and a Growth/Differentiation Factor (GDF) family member, thereby inducing differentiation of the mesoderm into a plurality of chondrocytes;

pelleting the plurality of chondrocytes; and culturing under hypoxic conditions the pelleted plurality of chondrocytes in a fourth culture medium, thereby producing cartilage.

2. The method according to claim 1, wherein the pelleted plurality of chondrocytes is cultured under hypoxic conditions in the fourth culture media on a substrate.

3. The method according to claim 2, wherein the substrate comprises a porous membrane or cartilage.

4. A method for differentiating under hypoxic conditions pluripotent stem cells (PSCs) into chondrocytes, the method comprising:

providing PSCs;

culturing the PSCs under hypoxic conditions in a first culture medium comprising a Wingless/Integrated (WNT) family member, an Activin family member, and a Fibroblast Growth Factor (FGF) family member; member, thereby inducing differentiation of the PSCs into primitive streak/mesendoderm;

culturing the primitive streak/mesendoderm under hypoxic conditions in a second culture a medium comprising an FGF family member, a bone morphogenetic protein (BMP) family member, Follistatin, and a Neurotrophin (NT), thereby inducing differentiation of the primitive streak/mesendoderm into a mesoderm; and culturing the mesoderm under hypoxic conditions in a third culture medium comprising a FGF family member, a BMP family member, an NT, and a Growth/Differentiation Factor (GDF) family member.

5. The method according to claim 1, wherein the third culture medium further comprises a transforming growth factor-β (TGF-β) subfamily member.

6. The method according to claim 1, further comprising removing an undifferentiated PSC from the plurality of chondrocytes prior to pelleting.

7. The method according to claim 6, wherein the removal comprises passaging the plurality of chondrocytes and culturing the passaged plurality of chondrocytes on tissue culture plastic.

8. The method according to claim 4, further comprising culturing the plurality of chondrocytes as a pellet.

9. The method according to claim 1, wherein the PSCs comprise embryonic stem cells (ESCs) or induced pluripotent stem cells (iPSCs).

10. The method according to claim 1, wherein the PSCs are cultured under hypoxic conditions in the first culture medium for 2 to 6 days.

11. The method according to claim 1, wherein the first culture medium comprises WNT3A, Activin A, and FGF2.

12. The method according to claim 1, wherein the primitive streak/mesendoderm is cultured under hypoxic conditions in the second culture medium for 3 to 7 days.

13. The method according to claim 1, wherein the second culture medium comprises FGF2, Follistatin, BMP4, and NT4.

14. The method according to claim 1, wherein the mesoderm is cultured under hypoxic conditions in the third culture medium for about 5 days.

15. The method according to claim 1, wherein the mesoderm is cultured under hypoxic conditions in the third culture medium for 4 to 6 days.

16. The method according to claim 1, wherein the third culture medium comprises FGF2, BMP4, NT4, and GDF5.

17. The method according to claim 1, further comprising filtering the plurality of chondrocytes prior to pelleting.

18. The method according to claim 8, wherein the plurality of chondrocytes are cultured as a pellet under hypoxic conditions.

19. A method of repairing or replacing damaged cartilage in a subject in need thereof comprising implanting an effective amount of the cartilage produced by the method according to claim 1.

* * * * *